United States Patent
Roch et al.

(12) 
(10) Patent No.: US 6,653,102 B2
(45) Date of Patent: Nov. 25, 2003

(54) NUCLEIC ACID ENCODING A PHOSPHATASE 2C THAT INTERACTS WITH FE 65

(75) Inventors: Jean-Marc Roch, Salt Lake City, UT (US); Paul L. Bartel, Salt Lake City, UT (US); Karen Heichman, Salt Lake City, UT (US); Kimberly Mauck, Sandy, UT (US); Max Dufford, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 0 days.

(21) Appl. No.: 09/973,963

(22) Filed: Oct. 11, 2001

(65) Prior Publication Data

US 2002/0106676 A1 Aug. 8, 2002

Related U.S. Application Data

(60) Provisional application No. 60/304,775, filed on Jul. 13, 2001, and provisional application No. 60/240,790, filed on Oct. 17, 2000.

(51) Int. Cl.$^7$ .................. C12N 15/00; C12N 15/63; C12N 15/85; C12N 9/00; C07H 21/04
(52) U.S. Cl. ................. 435/69.1; 435/320.1; 435/325; 435/252.3; 435/254.11; 435/254.2; 435/183; 536/23.5
(58) Field of Search .................. 536/23.1, 23.5; 435/320.1, 325, 252.3, 254.11, 254.2, 69.1; 530/350

(56) References Cited

FOREIGN PATENT DOCUMENTS

| WO | WO 00/55174 A1 | * | 9/2000 |
| WO | WO 01/96546 A2 | | 12/2001 |
| WO | WO 01/96571 A2 | | 12/2001 |

OTHER PUBLICATIONS

McLoughlin et al, The intracellular cytoplamic domain of the Alzheimer'disease amyloid precursor protein interacts with phosphotyrosine–binding domain proteins in the yeast two–hybrid system. FEBS Letters 397:197–200, 1996.*

Borg et al, The phosphotyrosine interaction domains of X11 and FE65 bind to distinct sites on the YENPTY motif of amyloid precursor protein. Mol. Cell. Biol.*

Choi et al, Phosphorylation of stargazin by protein kinase A regulates its interaction with PSD–95. J. Biol. Chem. 277:12359–12363, 2002.*

Palmer et al, Interaction of the peroxisome proliferator–activated receptor alpha with the retinoid X receptor alpha unmasks a cryptic peroxisome proliferator response element that overlaps an ART–1–binding site in the CYP4A6 Promoter. J. Biol. Chem. 269: 18083–18089, 1994.*

Rain et al, The protein–protein interaction map of Helicobacter Pylori. Nature 409:211–215, 2000.*

Birren et al, GenBank, Accession No. AC013612, Apr. 3, 2000.*

Dmitrenko et al, GenBank, Accession No. Z69892, Mar. 4, 1996.*

Zambrano et al, Interaction of the Phosphotyrosine Interaction/Phosphotyrosine Binding–related Domains of Fe65 with Wild–type and Mutant Alzheimer's–Amyloid Proteins. J. Biol. Chem. 272:6399–6405, 1997.*

Zambrano et al, The Fe65 Adaptor Protein Interacts through Its PID1 Domain with the Transcription Factor CP2/LSF/LBP1. J. Biol. Chem. 273:20128–20133, 1998.*

* cited by examiner

Primary Examiner—Yvonne Eyler
Assistant Examiner—Ruixiang Li
(74) Attorney, Agent, or Firm—Jonathan Baker; Myriad Ip Dept.

(57) ABSTRACT

The present invention relates to the discovery of protein—protein interactions that are involved in the pathogenesis of neurodegenerative disorders, including Alzheimer's disease (AD). Thus, the present invention is directed to complexes of these proteins and/or their fragments, antibodies to the complexes, diagnosis of neurodegenerative disorders (including diagnosis of a predisposition to and diagnosis of the existence of the disorder), drug screening for agents which modulate the interaction of proteins described herein, and identification of additional proteins in the pathway common to the proteins described herein.

4 Claims, No Drawings

NUCLEIC ACID ENCODING A PHOSPHATASE 2C THAT INTERACTS WITH FE 65

CROSS-REFERENCE TO RELATED APPLICATIONS

The present application is related to U.S. provisional patent application Serial No. 60/240,790, filed on Oct. 17, 2000 and Serial No. 60/304,775 filed on July 13, 2001, each incorporated herein by reference, and claims priority thereto under 35 USC §119(e).

BACKGROUND OF THE INVENTION

The present invention relates to the discovery of protein—protein interactions that are involved in the pathogenesis of neurodegenerative disorders, including Huntington's Disease, Parkinson's Disease, dementia and Alzheimer's Disease (AD). Thus, the present invention is directed to complexes of these proteins and/or their fragments, antibodies to the complexes, diagnosis of neurodegenerative disorders (including diagnosis of a predisposition to and diagnosis of the existence of the disorder), drug screening for agents which modulate the interaction of proteins described herein, and identification of additional proteins in the pathway common to the proteins described herein.

The publications and other materials used herein to illuminate the background of the invention, and in particular, cases to provide additional details respecting the practice, are incorporated herein by reference, and for convenience, are referenced by author and date in the following text and respectively grouped in the appended Bibliography.

Alzheimer's Disease (AD) is a neurodegenerative disease characterized by a progressive decline of cognitive functions, including loss or declarative and procedural memory, decreased learning ability, reduced attention span, and severe impairment in thinking ability, judgment, and decision making. Mood disorders and depression are also often observed in AD patients. It is estimated that AD affects about 4 million people in the USA and 20 million people world wide. Because AD is an age-related disorder (with an average onset at 65 years), the incidence of the disease in industrialized countries is expected to rise dramatically as the population of these countries is aging.

AD is characterized by the following neuropathological features:
- a massive loss of neurons and synapses in the brain regions involved in higher cognitive functions (association cortex, hippocampus, amygdala). Cholinergic neurons are particularly affected.
- neuritic (senile) plaques that are composed of a core of amyloid material surrounded by a halo of dystrophic neurites, reactive type I astrocytes, and numerous microglial cells (Selkoe, 1994a; Selkoe, 1994c; Dickson, 1997; Hardy and Gwinn-Hardy, 1998; Selkoe, 1996b). The major component of the core is a peptide of 39 to 42 amino acids called the amyloid β protein, or Aβ. Although the Aβ protein is produced by the intracellular processing of its precursor, APP, the amyloid deposits forming the core of the plaques are extracellular. Studies have shown that the longer form of Aβ (Aβ42) is much more amyloidogenic than the shorter forms (Aβ40 or Aβ39).
- neurofibrillary tangles that are composed of paired-helical filaments (PHF) (Ray et al., 1998; Brion, 1998). Biochemical analyses revealed that the main component of PHF is a hyper-phosphorylated form of the microtubule-associated protein τ. These tangles are intracellular structures, found in the cell body of dying neurons, as well as some dystrophic neurites in the halo surrounding neuritic plaques.

Both plaques and tangles are found in the same brain regions affected by neuronal and synaptic loss.

Although the neuronal and synaptic loss is universally recognized as the primary cause of the decline of cognitive functions, the cellular, biochemical, and molecular events responsible for this neuronal and synaptic loss are subject to fierce controversy. The number of tangles shows a better correlation than the amyloid load with the cognitive decline (Albert, 1996). On the other hand, a number of studies showed that amyloid can be directly toxic to neurons (Iversen et al., 1995; Weiss et al., 1994; Lorenzo and Yankner, 1996; Storey and Cappai, 1999), resulting in behavioral impairment (Ma et al., 1996). It has also been shown that the toxicity of some compounds (amyloid or tangles) could be aggravated by activation of the complement cascade (Rogers et al., 1992b; Rozemuller et al., 1992; Rogers et al., 1992a; Webster et al., 1997), suggesting the possible involvement of inflammatory process in the neuronal death (Fagarasan and Aisen, 1996; Kalaria et al., 1996b; Kalaria et al., 1996a; Farlow, 1998).

Genetic and molecular studies of some familial forms of AD (FAD) have recently provided evidence that boosted the amyloid hypothesis (Ii, 1995; Price et al., 1995; Hardy, 1997; Selkoe, 1996a). The assumption is that since the deposition of Aβ in the core of senile plaques is observed in all Alzheimer cases, if Aβ is the primary cause of AD, then mutations that are linked to FAD should induce changes that, in a way or another, foster Aβ deposition. There are 3 FAD genes known so far (Hardy and Gwinn-Hardy, 1998; Ray et al., 1998), and the activity of all of them results in increased Aβ deposition, a very compelling argument in favor of the amyloid hypothesis.

The first of the 3 FAD genes codes for the Aβ precursor, APP (Selkoe, 1996a). Mutations in the APP gene are very rare, but all of them cause AD with 100% penetrance and result in elevated production of either total Aβ or Aβ42, both in vitro (transfected cells) and in vivo (transgenic animals). The other two FAD genes code for presenilin 1 and 2 (PS1, PS2) (Hardy, 1997). The presenilins contain 8 transmembrane domains and several lines of evidence suggest that they are involved in intracellular protein trafficking, although other studies suggest that they could function as proteases (see below). Mutations in the presenilin genes are more common than in the APP genes, and all of them also cause FAD with 100% penetrance. In addition, in vitro and in vivo studies have demonstrated that PS1 and PS2 mutations shift APP metabolism, resulting in elevated Aβ42 production. For a recent review on the genetics of AD, see (Lippa, 1999).

In spite of these compelling genetic data, it is still unclear whether Aβ generation and amyloid deposition are the primary cause of neuronal death and synaptic loss observed in AD. Moreover, the biochemical events leading to Aβ production, the relationship between APP and the presenilins, and between amyloid and neurofibrillary tangles are poorly understood. Thus, the picture of interactions between the major Alzheimer proteins is very incomplete, and it is clear that a large number of novel proteins are yet to be discovered. To this end, we have initiated a systematic study looking at proteins interacting with various domains of the major Alzheimer proteins (see below). The results from these experiments provide a more complete understanding of the protein—protein interactions involved in AD pathogenesis, and thus will greatly help in the identification of a drug target. Because AD is a neurodegenerative disease, it is also expected that this project will identify novel proteins involved in neuronal survival, neurite outgrowth, and maintenance of synaptic structures, thus opening opportunities into potentially any pathological condition in which the integrity of neurons and synapses is threatened.

Thus, the picture of interactions between the major AD proteins is very incomplete, and it is clear that a number of novel proteins are yet to be discovered. Although a number of molecules have been identified as possibly involved in the disease progression, no particular protein (or set of proteins) has been identified as primarily responsible for the loss of neurons and synapses. More importantly, none of the various components identified so far in the cascade of events leading to AD is a confirmed drug target.

There continues to be a need in the art for the discovery of additional proteins interacting with various domains of the major Alzheimer proteins, including APP and the presenilins. There continues to be a need in the art also to identify the protein—protein interactions that are involved in AD pathogenesis, and to thus identify drug targets.

SUMMARY OF THE INVENTION

The present invention relates to the discovery of protein—protein interactions that are involved in the pathogenesis of neurodegenerative disorders, including AD, and to the use of this discovery. The identification of the AD interacting proteins described herein provide new targets for the identification of useful pharmaceuticals, new targets for diagnostic tools in the identification of individuals at risk, sequences for production of transformed cell lines, cellular models and animal models, and new bases for therapeutic intervention in neurodegenerative disorders, including AD.

Thus, one aspect of the present invention are protein complexes. The protein complexes are a complex of (a) two interacting proteins, (b) a first interacting protein and a fragment of a second interacting protein, (c) a fragment of a first interacting protein and a second interacting protein, or (d) a fragment of a first interacting protein and a fragment of a second interacting protein. The fragments of the interacting proteins include those parts of the proteins, which interact to form a complex. This aspect of the invention includes the detection of protein interactions and the production of proteins by recombinant techniques. The latter embodiment also includes cloned sequences, vectors, transfected or transformed host cells and transgenic animals.

A second aspect of the present invention is an antibody that is immunoreactive with the above complex. The antibody may be a polyclonal antibody or a monoclonal antibody. While the antibody is immunoreactive with the complex, it is not immunoreactive with the component parts of the complex. That is, the antibody is not immunoreactive with a first interactive protein, a fragment of a first interacting protein, a second interacting protein or a fragment of a second interacting protein. Such antibodies can be used to detect the presence or absence of the protein complexes.

A third aspect of the present invention is a method for diagnosing a predisposition for neurodegenerative disorders in a human or other animal. The diagnosis of a neurodegenerative disorder includes a diagnosis of a predisposition to a neurodegenerative disorder and a diagnosis for the existence of a neurodegenerative disorder. In a preferred embodiment, the diagnosis is for AD. In accordance with this method, the ability of a first interacting protein or fragment thereof to form a complex with a second interacting protein or a fragment thereof is assayed, or the genes encoding interacting proteins are screened for mutations in interacting portions of the protein molecules. The inability of a first interacting protein or fragment thereof to form a complex, or the presence of mutations in a gene within the interacting domain, is indicative of a predisposition to, or existence of a neurodegenerative disorder, such as AD. In accordance with one embodiment of the invention, the ability to form a complex is assayed in a two-hybrid assay. In a first aspect of this embodiment, the ability to form a complex is assayed by a yeast two-hybrid assay. In a second aspect, the ability to form a complex is assayed by a mammalian two-hybrid assay. In a second embodiment, the ability to form a complex is assayed by measuring in vitro a complex formed by combining said first protein and said second protein. In one aspect the proteins are isolated from a human or other animal. In a third embodiment, the ability to form a complex is assayed by measuring the binding of an antibody, which is specific for the complex. In a fourth embodiment, the ability to form a complex is assayed by measuring the binding of an antibody that is specific for the complex with a tissue extract from a human or other animal. In a fifth embodiment, coding sequences of the interacting proteins described herein are screened for mutations.

A fourth aspect of the present invention is a method for screening for drug candidates which are capable of modulating the interaction of a first interacting protein and a second interacting protein. In this method, the amount of the complex formed in the presence of a drug is compared with the amount of the complex formed in the absence of the drug. If the amount of complex formed in the presence of the drug is greater than or less than the amount of complex formed in the absence of the drug, the drug is a candidate for modulating the interaction of the first and second interacting proteins. The drug promotes the interaction if the complex formed in the presence of the drug is greater and inhibits (or disrupts) the interaction if the complex formed in the presence of the drug is less. The drug may affect the interaction directly, i.e., by modulating the binding of the two proteins, or indirectly, e.g., by modulating the expression of one or both of the proteins.

A fifth aspect of the present invention is a model for neurodegenerative disorders, including AD. The model may be a cellular model or an animal model, as further described herein. In accordance with one embodiment of the invention, an animal model is prepared by creating transgenic or "knock-out" animals. The knock-out may be a total knock-out, i.e., the desired gene is deleted, or a conditional knock-out, i.e., the gene is active until it is knocked out at a determined time. In a second embodiment, a cell line is derived from such animals for use as a model. In a third embodiment, an animal model is prepared in which the biological activity of a protein complex of the present invention has been altered. In one aspect, the biological activity is altered by disrupting the formation of the protein complex, such as by the binding of an antibody or small molecule to one of the proteins which prevents the formation of the protein complex. In a second aspect, the biological activity of a protein complex is altered by disrupting the action of the complex, such as y the binding of an antibody or small molecule to the protein complex which interferes with the action of the protein complex as described herein. In a fourth embodiment, a cell model is prepared by altering the genome of the cells in a cell line. In one aspect, the genome of the cells is modified to produce at least one protein complex described herein. In a second aspect, the genome of the cells is modified to eliminate at least one protein of the protein complexes described herein.

A sixth aspect of the present invention are nucleic acids coding for novel proteins discovered in accordance with the present invention.

A seventh aspect of the present invention is a method for screening for drug candidates useful for treating a physiological disorder. In this embodiment, drugs are screened on the basis of the association of a protein with a particular physiological disorder. This association is established in accordance with the present invention by identifying a relationship of the protein with a particular physiological disorder. The drugs are screened by comparing the activity of the protein in the presence and absence of the drug. If a difference in activity is found, then the drug is a drug candidate for the physiological disorder. The activity of the protein can be assayed in vitro or in vivo using conventional techniques, including transgenic animals and cell lines of the present invention.

DETAILED DESCRIPTION OF THE INVENTION

The present invention is the discovery of novel interactions between PS1, APP or other protein involved in AD and other proteins. The genes coding for these proteins have been cloned previously, but their potential involvement in AD was unknown. These proteins play a major role in AD and neurodegeneration, based in part on the discovery of their interactions and on their known biological functions. These proteins were identified using the yeast two-hybrid method and searching a human total brain library, as more filly described below.

Although the senile plaque density and amyloid load do not correlate with cognitive decline, the genetic data strongly support a causal involvement of amyloid production in AD pathogenesis (Neve et al., 1990; Selkoe, 1994a; Octave, 1995; Roch et al., 1993; Saitoh, Roch, 1995; Selkoe, 1994b; Selkoe, 1996a). The 3 genes identified so far that contain mutations known to cause AD are APP, PS1 and PS2.Because the number of AD mutations found in PS1 (over 50) is much larger than the number of AD mutations found in PS2 (only 2), most of the studies looking at the involvement of the presenilins in AD have focused on PS1 rather than PS2. As for APP, although the number of AD mutations in the APP gene is small (5), the mere fact the APP is the biochemical precursor of A$\beta$ put it in the heart of countless studies world wide. Thus, it is no surprise that the APP and PS1 gene products are always found as the major components of the description of events leading to neuronal death.

APP refers to a group of transmembrane proteins translated from alternatively spliced mRNAs. The smallest isoform contains 695 amino acids and is expressed almost exclusively in the brain, where it is the major APP isoform. The other major isoforms, of 714, 751, and 770 residues, contain either one or both domains of 19 and 51 residues with homology to the OX-2 antigen and Kunitz type protease inhibitors, respectively. The metabolism of APP is complex, following several different pathways. APP can be secreted from cells such as PC12, fibroblasts, and neurons. The secretion event includes a cleavage step of the precursor, releasing a large N-terminal portion of APP, sAPP, into the medium. The majority of cleavage is at the $\alpha$-secretase site and occurs within the A$\beta$ domain between amino acids $\beta$16 and $\beta$17, and releases sAPP$\alpha$ extracellularly. Thus, the processing of APP through the $\alpha$-secretory pathway precludes the formation of intact A$\beta$ protein. APP can also follow a pathway that leads to the secretion of A$\beta$ protein, as well as sAPP$\beta$, which is 15 amino acids shorter than sAPP$\alpha$. Clearly, this pathway is potentially amyloidogenic. However, the secretion of A$\beta$ protein is not the result of an aberrant processing of APP because it occurs in cultured cells under normal physiological conditions, and secreted A $\beta$ protein has been detected in biological fluids from normal individuals. The regulation of these two pathways involves both PKC-dependent and PKC-independent phosphorylation reactions and is also altered by some of the mutations within the APP molecule that cause AD in some Swedish families (see below).

Recently, the enzyme that cleaves APP at the $\beta$ site (D597 of APP695) has been identified and its cDNA cloned (Vassar et al., 1999; Hussain et al., 1999). This $\beta$-secretase enzyme, called BACE or Asp-2, is a transmembrane protein of 501 residues which belongs to the Aspartyl Protease family. Although BACE is clearly able to cleave APP at the $\beta$ site, it is unclear whether APP is the natural physiological substrate of BACE. Cleavage of APP at the a site results in the secretion of sAPP$\alpha$ and recycling of an 83-residue non-amyloidogenic transmembrane C-terminal fragment, C83. Cleavage of APP at the $\beta$ site results in the secretion of sAPP$\beta$ and recycling of an 99-residue potentially amyloidogenic transmembrane C-terminal fragment, C99. After cleavage of the precursor at the $\alpha$ or $\beta$ site, C83 and C99 can be further cleaved at the so called $\gamma$ site (APP636 to APP638), thus releasing the p3 fragment or the A$\beta$ peptide, respectively.

Recent studies suggest that PS1 and PS2 are capable of cleaving APP at the $\gamma$ site (Wolfe et al., 1999b; De Strooper et al., 1999; Wolfe et al., 1999a; Li et al.2000a; Li et al. 2000b). However, it is still unclear whether PS 1 and PS2 are the only potential $\gamma$-secretases, or they function as part of a large molecular complex or as purified proteins. It has recently been suggested that different $\gamma$-secretase activities occur in different cellular compartments (Murphy et al., 1999), and that PS1 might in fact regulate these pharmacologically distinct enzymatic activities (Murphy et al. 2000). The fact that the presenilins are often found inside the cells as part of large molecular complex (Zhou et al., 1997b; Yu et al., 1998; Thinakaran et al., 1997; Yu et al. 2000a)} suggests that other proteins are involved in the $\gamma$-secretase activity. Recently, a novel protein named nicastrin that binds both PS1 and PS2 as well as APP was shown to modulate the presenilin-mediated cleavage of APP at the $\gamma$ site (Yu et al., 2000b). Thus, the exact function of the presenilins in APP processing is not yet fully understood. The double mutation located just upstream of the $\beta$-cleavage site (known as the "Swedish" mutation) was shown to shift the metabolism of APP from the $\alpha$-secretase toward the $\beta$-secretase pathway, thus increasing the production of total A$\beta$. On the other hand, the Val717 mutations, located just after the $\gamma$ cleavage site do not alter the ratio of $\alpha$ vs $\beta$ cleavage, but increase the ratio of A$\beta$42 vs total A$\beta$, thus making more of the highly amyloidogenic form. Therefore, both types of mutations alter the metabolism of APP in a way that results in elevated levels of A$\beta$42, thus fostering amyloid formation. For reviews on APP processing and its involvement in AD, see (Ashall and Goate, 1994; Selkoe, 1994a; Hardy, 1997; Selkoe, 1994b; Roch and Puttfarcken, 1996; Storey and Cappai, 1999; Haass and De Strooper, 1999; Wolfe et al., 1999a; Selkoe, 1999).

There is contradicting evidence as to the cellular location where APP is cleaved by the secretases (Price et al., 1995; Beyreuther et al., 1996; Leblanc et al., 1996; Caputi et al., 1997; Selkoe, 1997). Some investigators suggested that APP is cleaved in the trans-Golgi network (TGN) or in secretory vesicles en route to the plasma membrane, while others presented evidence that intact APP reaches the plasma membrane and is cleaved only after it is expressed at the cell surface. Different cell types and expression systems could explain those discrepancies. However, it is now well established that either full-length APP or its C-terminal fragment are recycled into the endosomal-lysosomal compartment. The C-terminal fragments that contain the complete Aβ domain are transported further back to the TGN and endoplasmic reticulum, where Aβ40 and Aβ42 are produced, respectively. The free Aβ fragments are then re-routed again toward the cell surface through secretory vesicles, and ultimately secreted into the extracellular milieu, where the Aβ42 will seed the aggregation into amyloid material. Clearly, proteins that interact with the cytoplasmic tail of APP could play a major role in its intracellular traffic, thus its metabolism. The cytoplasmic domain of APP was shown to interact with intracellular proteins Fe65, Fe65L, X11, and X11L (McLoughlin and Miller, 1996; Blanco et al., 1998; Russo et al., 1998; Trommsdorff et al., 1998). These proteins have been localized in both the cytosol and the nucleus (Zambrano et al., 1998) and are thought to play a role in transcription regulation. In fact, Fe65 is known to interact with know transcription factors Mena and LSF (Zambrano et al., 1998; Ermekova et al., 1997). There is also ample evidence that Fe65 and LSF influence the intracellular trafficking of APP, and thus indirectly control APP metabolism (Russo et al., 1998; Sabo et al., 1999), a central event in AD pathogenesis.

The mechanism of Aβ toxicity is also highly controversial (Iversen et al., 1995; Manelli and Puttfarcken, 1995; Gillardon et al., 1996; Behl et al., 1992; Weiss et al., 1994; Octave, 1995; Furukawa et al., 1996a; Schubert, 1997). Some studies indicate that Aβ must be in the aggregated amyloid form to be toxic. Other investigators showed that soluble Aβ is toxic and suggested that aggregation of soluble Aβ into amyloid fibrils is a defense mechanism aiming at sequestering soluble Aβ. While most studies found that Aβ is toxic to cells from the outside, a few investigators also found that Aβ can kill cells from the inside, before it is secreted. Whatever the exact mechanism is, a consensus is now emerging, indicating that Aβ disrupts calcium homeostasis and triggers the generation of free radicals and lipid peroxidation (Weiss et al., 1994; Abe and Kimura, 1996; Mark et al., 1997; Kruman et al., 1997). Consistent with this idea, antioxidants (such as vitamin E) and neurotrophic factors that attenuate calcium influx (such as sAPP) protect neurons from Aβ mediated toxicity (Behl et al., 1992; Weiss et al., 1994).

After cleavage by the α- or β-secretase, the N-terminal portion of APP is secreted into the extracellular milieu where it shows a wide variety of functions. The most relevant to AD are the neurotrophic and neuroprotective activities. A number of in vitro studies have shown that sAPP stimulates cell growth (Ninomiya et al., 1993; Roch et al., 1992; Saitoh et al., 1989; Pietrzik et al., 1998), neurite extension (Milward et al., 1992; Ninomiya et al., 1994; Araki et al., 1991; Jin et al., 1994; Yamamoto et al., 1994; Small et al., 1994; Li et al., 1997), neuronal survival (Mattson et al., 1995; Yamamoto et al., 1994; Furukawa et al., 1996b; Barger et al., 1995), and protects neurons from various toxic insults (including glucose and/or oxygen deprivation, gp120, glutamate, Aβ) (Mattson et al., 1993a; Mattson et al., 1993b; Barger and Mattson, 1996; Guo et al., 1998b). The biochemical and cellular events underlying those in vitro activities have not been elucidated yet, however it appears that sAPP function is probably carried out by receptor mediated mechanisms and activation of a signal transduction cascade. Binding sites for sAPP were found on the surface of neuroblastoma cells, and the binding affinity was in the same range of optimal concentration (10 nM) for neurite outgrowth (Ninomiya et al., 1994; Jin et al., 1994).

Depending on the target cells and the experimental paradigm, sAPP was found to elicit various cellular responses that include activation of potassium channels (Furukawa et al., 1996a), activation of a membrane associated guanylate cyclase (Barger and Mattson, 1995), induction of NF-kappa B dependent transcription (Barger and Mattson, 1996), increase in phosphatidyl inositol turnover (Jin et al., 1994), and changes in the phosphotyrosine balance (Wallace et al., 1997b; Wallace et al., 1997a; Saitoh et al., 1995; Mook-Jung and Saitoh, 1997). Specifically, it was found that sAPP neurite extension activity on neuroblastoma was stimulated by genistein, a tyrosine kinase inhibitor, while orthovanadate, a phosphotyrosine phosphatase inhibitor, abolished sAPP effects (Saitoh et al., 1995). This suggests that tyrosine dephosphorylation is involved in sAPP action. On the other hand, in a different experimental paradigm, sAPP was shown to activate tyrosine phosphorylation (Wallace et al., 1997b; Wallace et al., 1997a; Mook-Jung and Saitoh, 1997), which could be the result of either inhibition of a tyrosine phosphatase, or activation of a tyrosine kinase. In any event, it is clear that sAPP modulates the balance of intracellular phosphotyrosine content. These in vitro activities are reflected in vivo by a stabilization of synaptic structures in the brain (Roch et al., 1994). In addition, sAPP protected brain neurons against various injuries (Mucke et al., 1995; Masliah et al., 1997) and provided neurological protection against ischemia in brain and spinal cord (Smith-Swintosky et al., 1994; Bowes et al., 1994; Komori et al., 1997). Most importantly, these protective and trophic activities at the cellular level are reflected at the behavioral level by memory and cognitive enhancement. Specifically, sAPP was shown to increase memory retention in rats (Roch et al., 1994; Gschwind et al., 1996; Huber et al., 1997) and mice (Meziane et al., 1998), and conversely, compromising the function of sAPP resulted in memory and learning impairment (Huber et al., 1993; Doyle et al., 1990). The site of sAPP that is responsible for the trophic activity was mapped to a domain of 17 amino acids, from Ala319 to Met332. This peptide was shown to stimulate cell growth, to bind to neuroblastoma cells and trigger neurite extension, to enhance neuronal survival, synaptic stability, and memory retention (Roch et al., 1994; Ninomiya et al., 1994; Jin et al., 1994; Ninomiya et al., 1993; Yamamoto et al., 1994). Furthermore, this sAPP peptide was shown to elicit the same cellular responses as sAPP itself, namely the increase in phosphatidyl inositol turnover (Jin et al., 1994) and changes in tyrosine phosphorylation (Saitoh et al., 1995; Mook-Jung and Saitoh, 1997). In brief, there is now mounting evidence for a neurotrophic and neuroprotective function of sAPP, which is reflected by increased learning and memory performance.

A few years ago, two new Alzheimer genes were discovered, coding for PS1 and PS2 (Hardy, 1997; Hardy and Gwinn-Hardy, 1998; Ray et al., 1998). These two proteins share 67% identity and although a number of studies report a topological structure with 6 to 9 transmembrane domains, a consensus is now emerging for a structure with 8 transmembrane domains (Doan et al., 1996; Lehmann et al., 1997; Hardy, 1997). Although their exact function is not known, they appear to be involved in intracellular protein trafficking. Thus, presenilins are potentially implicated in APP metabolism. This hypothesis is supported by numerous in vitro and in vivo studies showing that the AD mutations in PS1 and PS2 alter APP metabolism resulting in elevated production of Aβ42, although the total Aβ was not changed (Duff et al., 1996; Lemere et al., 1996; Borchelt et al., 1996; Tomita et al., 1997; Ishii et al., 1997; Oyama et al., 1998; Hutton and Hardy, 1997; Cruts, Van Broeckhoven, 1998; Kim and Tanzi, 1997; Hardy, 1997; Citron et al., 1998).

The possibility that PS1 and PS2 function as APP cleaving enzymes at the γ site was recently raised by a number of investigators (De Strooper et al., 1999; Wolfe et al., 1999a; Sinha and Lieberburg, 1999; Annaert et al., 1999; Haass and De Strooper, 1999), although other studies suggest that the presenilins control the activity of γ-secretase(s) rather than cleave APP directly (Murphy et al., 2000; Murphy et al., 1999). Still, the mere fact that AD mutations in proteins other than APP itself also result in increased production of Aβ42 is a compelling argument in favor of the amyloid hypothesis. Additionally, mutations in PS1 and PS2 have been shown to be neurotoxic through an apoptotic mechanism that is independent of amyloid production, notably the generation of superoxide and disruption of calcium homeostasis (Vito et al., 1996; Wolozin et al., 1996; Zhang et al., 1998; Renbaum and Levy-Lahad, 1998; Guo et al., 1998b; Mattson, 1997b; Guo et al., 1999a; Guo et al., 1999b; Guo et al., 1996). Recent studies have shown that the presenilins bind to several proteins of the Armadillo family, including δ-catenin, δ-catenin, and p0071(Yu et al., 1998; Murayama et al., 1998; Zhou et al., 1997a; Levesque et al., 1999; Tanahashi and Tabira, 1999; Stahl et al., 1999). The biological significance of these interactions is not clear, although recent studies suggest that FAD presenilin mutations disrupt the normal interaction pattern of the Armadillo proteins, and lead neuronal apoptosis (Zhang et al., 1998; Tesco et al., 1998). For example, the presence of PS1 and β-catenin in the same complex could influence the ultimate fate of β-catenin and its involvement with axin, GSK3-β, and PP2A in the wingless signaling pathway (Nakamura et al., 1998; Kosik, 1999; Dierick and Bejsovec, 1999). Conceivably, FAD associated mutations in PS1 could disrupt the PS1-β-catenin complex, resulting in aberrant β-catenin mediated signalling and eventual neuronal death.

In brief, there is now growing evidence that APP metabolism and Aβ generation are central events to AD pathogenesis, and that mutations in the presenilins can induce neuronal apoptosis as well as stimulate amyloid deposition. However, many obscure points remain. Although a candidate β-secretase enzyme has been identified (BACE), its normal physiological substrate is not known. The is same statement is also true for the γ-secretase: although PS1 and PS2 are strong candidates for the identity of γ-secretase, it remains the be determined if they function as catalytic or regulatory components of the γ-secretase complex, and what is their natural physiological substrate. Even less is known about the α-secretase, the enzyme that cleaves APP at the a site and thus precludes Aβ formation. The proteins that mediate the neurotrophic and neuroprotective effects of sAPP are unknown. This last point is of utmost importance because an alteration of APP metabolism could result in both the generation of a toxic product (Aβ) and the impairment of sAPP trophic activity (Saitoh et al., 1994; Roch et al., 1993; Saitoh and Roch, 1995). In this respect, it is interesting that one APP mutation associated with Alzheimer's results in a defective neurite extension activity of sAPP (Li et al., 1997). Moreover, the balance of phosphorylation cascades is deeply altered in Alzheimer brains (Saitoh and Roch, 1995; Jin and Saitoh, 1995; Mook-Jung and Saitoh, 1997; Saitoh et al., 1991; Shapiro et al., 1991). Because hyperphosphorylation of the microtubule-associated protein τ is necessary for the formation of paired helical filaments and tangles, a disruption of the phosphorylation cascade could be the link between the amyloid and the τ pathways.

Proteins that interact with sAPP are expected to be involved in its biological function, including neuron survival, synaptic formation and stability, learning and memory. Thus, it is expected that some of these will become promising targets for drugs designed to tackle AD and a number of other neurodegenerative conditions. Because sAPP showed obvious protective effects in ischemia models (Smith-Swintosky et al., 1994; Bowes et al., 1994; Mattson, 1997c; Komori et al., 1997), it is reasonable to assume that drugs that mimic sAPP function could be used to alleviate the effects of stroke (Mattson, 1997c). Likewise, the discovery of new proteins that interacts with the presenilins, δ-catenin, Fe65, or axin could establish previously unknown biochemical pathways, and identify drug targets that could influence APP metabolism, presenilin functions, neuronal survival, and synaptic maintenance. As mentioned above, cholinergic neurons are particularly affected and levels of acetylcholine are markedly reduced in AD brains compared to controls. To date, the only Alzheimer drugs available are inhibitors of acetylcholine esterase (AChE). This enzyme has also been found to be associated with neuritic plaques (Inestrosa and Alarcon, 1998) and to interact with APP (Alvarez et al., 1998). Thus, proteins that interact with ACHE also represent important opportunities for drug discovery in Alzheimer's disease.

According to the present invention, new protein—protein interactions have been discovered. The discovery of these interactions has identified several protein complexes for each protein—protein interaction. The protein complexes for these interactions are set forth below in Tables 1–33, which also identify the new protein—protein interactions of the present invention. The involvement of the protein—protein interactions in neurodegenerative disease is described below with reference to individual or grouped interactions.

TABLE 1

Protein Complexes of BAT3-Glypican Interaction

HLA-B associated transcript (BAT3) and glypican
A fragment of BAT3 and glypican
BAT3 and a fragment of glypican
A fragment of BAT3 and a fragment of glypican

TABLE 2

Protein Complexes of BAT3-LRP2 Interaction

HLA-B associated transcript (BAT3) and LRP2
A fragment of BAT3 and LRP2
BAT3 and a fragment of LRP2
A fragment of BAT3 and a fragment of LRP2

TABLE 3

Protein Complexes of BAT3-LRPAP1 Interaction

HLA-B associated transcript (BAT3) and LRPAP1
A fragment of BAT3 and LRPAP1
BAT3 and a fragment of LRPAP1
A fragment of BAT3 and a fragment of LRPAP1

TABLE 4

Protein Complexes of BAT3-Transthyretin Interaction

HLA-B associated transcript (BAT3) and transthyretin
A fragment of BAT3 and transthyretin
BAT3 and a fragment of transthyretin
A fragment of BAT3 and a fragment of transthyretin

TABLE 5

Protein Complexes of Fe65-PN7740 Interaction

Fe65 and PN7740
A fragment of Fe65 and PN7740
Fe65 and a fragment of PN7740
A fragment of Fe65 and a fragment of PN7740

TABLE 6

Protein Complexes of Mint1-GS Interaction

Mint1 and glutamine synthase (GS)
A fragment of Mint1 and GS
Minti and a fragment of GS
A fragment of Mint1 and a fragment of GS

TABLE 7

Protein Complexes of Mintl-KIAA0427 Interaction

Mint1 and KIAA0427
A fragment of Mint1 and KIAA0427
Minti and a fragment of KIAA0427
A fragment of Mint1 and a fragment of KIAA0427

TABLE 8

Protein Complexes of PS1-Mint1 Interaction

Presinilin 1 (PS1) and Mint1
A fragment of PS1 and Mint1
PS1 and a fragment of Mint1
A fragment of PS1 and a fragment of Mint1

TABLE 9

Protein Complexes of CASK-Dystrophin Interaction

CASK and dystrophin
A fragment of CASK and dystrophin
CASK and a fragment of dystrophin
A fragment of CASK and a fragment of dystrophin

TABLE 10

Protein Complexes of CIB-S1P Interaction

CIB and S1P
A fragment of CIB and S1P
CIB and a fragment of S1P
A fragment of CIB and a fragment of S1P

TABLE 11

Protein Complexes of Mint2-S1P Interaction

Mint2 and S1P
A fragment of Mint2 and S1P
Mint2 and a fragment of S1P
A fragment of Mint2 and a fragment of S1P

TABLE 12

Protein Complexes of PS1-P-glycerate DH Interaction

Presinilin 1 (PS1) and P-glycerate DH
A fragment of PS1 and P-glycerate DH
PS1 and a fragment of P-glycerate DH
A fragment of PS1 and a fragment of P-glycerate DH

TABLE 13

Protein Complexes of PS1-Beta-ETF Interaction

Presinilin 1 (PS1) and beta-ETF
A fragment of PS1 and beta-ETF
PS1 and a fragment of beta-ETF
A fragment of PS1 and a fragment of beta-ETF

TABLE 14

Protein Complexes of PS1-GAPDH Interaction

Presinilin 1 (PS1) and GAPDH
A fragment of PS1 and GAPDH
PS1 and a fragment of GAPDH
A fragment of PS1 and a fragment of GAPDH

TABLE 15

Protein Complexes of PS2-GAPDH Interaction

Presinilin 2 (PS2) and GAPDH
A fragment of PS2 and GAPDH
PS2 and a fragment of GAPDH
A fragment of PS2 and a fragment of GAPDH

TABLE 16

Protein Complexes of CIB-ATP synthase Interaction

CIB and ATP synthase
A fragment of CIB and ATP synthase
CIB and a fragment of ATP synthase
A fragment of CIB and a fragment of ATP synthase

TABLE 17

Protein Complexes of KIAA0443-PI-4-kinase Interaction

KIAA0443 and PI-4-kinase
A fragment of KIAA0443 and PI-4-kinase
KIAA0443 and a fragment of PI-4-kinase
A fragment of KIAA0443 and a fragment of PI-4-kinase

TABLE 18

Protein Complexes of KIAA0443-5HT-2A R Interaction

KIAA0443 and serotonin receptor 2A (5HT-2A R)
A fragment of KIAA0443 and 5HT-2A R
KIAA0443 and a fragment of 5HT-2A R
A fragment of KIAA0443 and a fragment of 5HT-2A R

TABLE 19

Protein Complexes of KIAAO35 1-TRIO Interaction

KIAA0351 and TRIO
A fragment of KIAA0351 and TRIO
KIAA0351 and a fragment of TRIO
A fragment of KIAAO351 and a fragment of TRIO

TABLE 20

Protein Complexes of CIB-MILK2 Interaction

CIB and MLK2
A fragment of CIB and MLK2
CIB and a fragment of MLK2
A fragment of CIB and a fragment of MLK2

TABLE 21

Protein Complexes of BAX-slo K$^+$ channel Interaction

BAX and slo K$^+$ channel
A fragment of BAX and slo K$^+$ channel
BAX and a fragment of slo K$^+$ channel
A fragment of BAX and a fragment of slo K$^+$ channel

TABLE 22

Protein Complexes of FAK2-SUR1 Interaction

Focal adhesion kinase 2 (FAK2) and SUR1
A fragment of FAK2 and SUR1
FAK2 and a fragment of SUR1
A fragment of FAK2 and a fragment of SUR1

TABLE 23

Protein Complexes of Mint2-PDE-9A Interaction

Mint2 and PDE-9A
A fragment of Mint2 and PDE-9A
Mint2 and a fragment of PDE-9A
A fragment of Mint2 and a fragment of PDE-9A

TABLE 24

Protein Complexes of CIB-SCD2 Interaction

CIB and SCD2
A fragment of CIB and SCD2
CIB and a fragment of SCD2
A fragment of CIB and a fragment of SCD2

TABLE 25

Protein Complexes of rab11-FAK Interaction carboxy-terminal region of rab-related GTP-binding protein 11 (rab11) and focal adhesion kinase (FAK)
A fragment of rab11 and FAK
rab11 and a fragment of FAK
A fragment of rab11 and a fragment of FAK

TABLE 26

Protein Complexes of FAK-Casein kinase II Interaction focal adhesion kinase (FAK) and casein kinase II
A fragment of FAK and casein kinase II
FAK and a fragment of casein kinase II
A fragment of FAK and a fragment of casein kinase II

TABLE 27

Protein Complexes of FAK-GST trans. M3 Interaction focal adhesion kinase (FAK) and GST trans. M3
A fragment of FAK and GST trans. M3
FAK and a fragment of GST trans. M3
A fragment of FAK and a fragment of GST trans. M3

TABLE 28

Protein Complexes of Bcr-PSD95 Interaction

Bcr and PSD95
A fragment of Bcr and PSD95
Bcr and a fragment of PSD95
A fragment of Bcr and a fragment of PSD95

TABLE 29

Protein Complexes of Bcr-DLG3 Interaction

Bcr and DLG3
A fragment of Bcr and DLG3
Bcr and a fragment of DLG3
A fragment of Bcr and a fragment of DLG3

TABLE 30

Protein Complexes of Bcr-Semaphorin F Interaction

Bcr and semaphorin F
A fragment of Bcr and semaphorin F
Bcr and a fragment of semaphorin F
A fragment of Bcr and a fragment of semaphorin F

TABLE 31

Protein Complexes of Bcr-HTF4A Interaction

Bcr and HTF4A
A fragment of Bcr and HTF4A
Bcr and a fragment of HTF4A
A fragment of Bcr and a fragment of HTF4A

TABLE 32

Protein Complexes of Bcr-SRCAP Interaction

Bcr and SRCAP
A fragment of Bcr and SRCAP
Bcr and a fragment of SRCAP
A fragment of Bcr and a fragment of SRCAP

TABLE 33

Protein Complexes of PSD95/PN7740 Interaction

PSD95 and PN7740
A fragment of PSD95 and PN7740
PSD95 and a fragment of PN7740
A fragment of PSD95 and a fragment of PN7740

APP metabolism is a critical event in the pathogenesis of Alzheimer's, because it leads to the release of either toxic (Aβ) or trophic (sAPP) metabolites (Cummings et al., 1998; Roch and Puttfarcken, 1996). In this respect, it is very important to identify proteins involved in the intracellular trafficking of APP. Proteins that interact with the cytosolic C-terminal region of APP play a major role in this process. The interaction of APP with Fe65, with Fe65 L, with Mint1, and with Mint2 have been well documented (Russo et al., 1998; Sastre et al., 1998). We also described an interaction between APP and BAT3, and between BAT3 and 6-adaptin, and we have explained the importance of these interactions in APP trafficking and metabolism (see U.S. patent application Ser. No. 09/466,139; International Patent Application No. PCT/U.S.99/30396 (WO 00/37483)), filed Dec. 21, 1999,). The presenilins (PS1 and PS2) are also involved in AD pathogenesis. Mutations in PS1 and PS2 are known to cause AD (Hardy, 1997; Selkoe, 1998), and recently, it was found that the presenilins could be the γ-secretase that cleave APP at the C-terminus of the Aβ peptide (Wolfe et al., 1999b; De Strooper et al., 1999; Wolfe et al., 1999a; Li et al., 2000a; Li et al., 2000b). PS1 interacts with δ-catenin (Zhou et al., 1997a; Tanahashi and Tabira, 1999) and CIB interacts with both PS1 and PS2 (Stabler et al., 1999). To extend our understanding of the role of these proteins in APP trafficking and metabolism, we have used some of the proteins mentioned above as baits in yeast two-hybrid searches.

Using a fragment of BAT from amino acids 271 to 480 as a bait in a yeast two-hybrid search, we found a clone encoding amino acids 400 to 483 of glypican as a prey. Glypican is one of the several core proteins of heparan sulfate proteoglycan (other core proteins include the various forms of syndecan, perlecan, appican, and others). The glypican cDNA codes for 558 residues, but after removal of the signal peptide (aa 1 to 23) and of the propeptide (aa 531 to 558), the mature form of glypican contains 507 amino acids. Glypican is attached to the membrane through a GPI anchor and was recently shown to be a receptor that mediates Ab toxicity (Schulz et al., 1998). On the other hand, secreted glypican binds to substrate-bound APP and inhibits neurite extension normally elicited by APP (Williamson et al., 1996). The mechanism of inhibition may be a competition of glypican for substrate-bound APP, against other endogenous proteoglycans that are normally required for APP to stimulate neurite outgrowth. In addition, because glypican bears heparan sulfate and because heparin stimulates β-secretase (Leveugle et al., 1997), glypican could favor release of sAPPβ vs sAPPα from cells, thus reducing the trophic potency of sAPP (sAPPβ is known to have greatly reduced neurite extension (Li et al., 1997) and neuroprotective (Furukawa et al., 1996b) activities compared to sAPPα). Thus, BAT3 interacts with both APP and glypican, which are known to interact with each other and control phenomenon such as neurite extension and neuronal survival. Pharmacological modulation of the BAT3-glypican interaction might influence the neurotrophic effects elicited by APP, as well as the neurotoxic effects mediated by Aβ.

Using a fragment of BAT3 from amino acids 740 to 1040 as a bait in a yeast two-hybrid search, we found a clone encoding amino acids 1 to 304 of LRP2 (LDL receptor related protein 2) as a prey. This protein (also called glycoprotein 330 and megalin) was shown to bind ApoJ (Kounnas et al., 1995), as well as ApoE (Orlando et al., 1997). A recent study (Zlokovic et al., 1996) suggested that LRP2 is necessary for the transport of ApoJ and ApoJ-Aβ1-40 complexes across the blood brain barrier, into the brain parenchyma. Another investigation (LaFerla et al., 1997) showed that intracellular accumulation of ApoE is correlated with the presence of intracellular Aβ in the same cytoplasmic granules, suggesting that uptake of lipids may have stabilized the hydrophobic Aβ protein within the cell. This work suggested a role for LRP2 in the ApoE uptake. Thus, LRP2 appears to be involved in the transport and stabilization of the Aβ protein. In this respect, the interactions of BAT3 with APP and LRP2 generates a biochemical link between APP and LRP2. We suggest that pharmacological modulation of the BAT3-LRP2 interaction might influence the transport and stabilization of the Aβ protein.

Using the same BAT3 bait, we also found a clone encoding amino acids 11 to 361 of LRPAP1 (LRP associated protein 1) as a prey. This protein was first isolated as a 39 kDa component of the alpha 2-macroglobulin (A2M) receptor complex (Striekland et al., 1991) and was called A2MRAP (for A2M receptor-associated protein), or MRAP, or simply RAP. Further studies (Korenberg et al., 1994; Van Leuven et al., 1995; Willnow et al., 1996; Willnow et al., 1995) showed that the human RAP gene (LRPAP1) is on chromosome 4p16.3. RAP, which is predominantly found in the endoplasmic reticulum, binds LRP1 and LRP2 and functions as a chaperone protein that selectively protects endocytic receptors (such as LRPs) by binding to newly synthesized receptor polypeptides, thereby preventing ligand-induced aggregation and subsequent degradation in the ER. In the light of the interaction between BAT3 and LRP2 (described above), it is important to note that A2M (a ligand for LRP1 and LRP2) binds to the Aβ domain of APP (Hughes et al., 1998). Thus, our finding suggest that BAT3 is an adaptor molecule that brings together APP and the components of the LRP-RAP-A2M complexes. A recent study has shown that ligand binding to receptor of the LDL receptor family triggers not only receptor internalization, but initiates a signal transduction cascade (Trommsdorff et al., 1998). Proteins such as Fe65 and DAB bind to the cytoplasmic tails of LRP, the LDL receptor, and APP, where they can potentially serve as molecular scaffolds for the assembly of cytosolic multiprotein complexes. The interaction pattern of BAT3 (with APP, LRP2, and LRPAP1) suggests a similar role. We suggest that pharmacological modulation of the BAT3-LRP2 and BAT3-LRPAP1 interactions might affect the signal transduction cascade elicited by these receptor molecules, and in turn, control APP trafficking and metabolism.

Using the same BAT3 bait, we also found a clone encoding amino acids 7 to 148 of transthyretin (TTH) as a prey. TTH is responsible for the transport of the thyroid hormone thyroxine from the bloodstream to the brain, is very abundant in the CSF (25% of total CSF protein) and, in the central nervous system, is synthesized exclusively by the epithelial cells of the choroid plexus. The active form is a homotetramer. Even before the identification of the Aβ protein, TTH was identified as a component of the neuritic plaques, neurofibrillary tangles, and cerebral vessel amyloid deposits (Shirahama et al., 1982). More recent studies have shown that TTH levels are reduced in the CSF of AD patients compared to age-matched controls (Merched et al., 1998), and TTH binding to Aβ inhibits amyloid fibrils in vitro (Schwarzman et al., 1994). Numerous variants in the transthyretin sequence are associated with various forms of amyloid polyneuropathy. Except for blood vessels, amyloid deposits are never found in the CNS. The interactions of BAT3 with APP, δ-adaptin (a lysosome targeting protein (see U.S. patent application Ser. No. 09/466,139; International Patent Application No. PCT/U.S. 99/30396 (WO 00/37483)), glypican (a mediator of Aβ toxicity, see above), LRP2 (transport and stabilization of the Aβ protein, see above), and now with TTH suggest a close involvement of BAT3 in AD pathogenesis. Similarly to the BAT3-LRP2 interaction, we suggest that pharmacological modulation of the BAT3-TTH interaction might influence the transport and stabilization of the Aβ protein.

Using a fragment of FE65 from amino acids 360 to 552 as a bait (the first phosphotyrosine binding domain, PTB), we found 3 clones coding for a novel protein. These clones have a coding capacity of 289 amino acids and contain stop codons in the other two reading frames. Sequence analysis of the novel protein fragment revealed the presence of a domain with high similarity to phosphatase 2C, from amino acids 78 to 289 of our insert. Using a variety of methods (RACE, arrayed library screening, plaque lifts), we extended the sequence of the cDNA encoding the novel protein, and found sequence containing a open reading frame (ORF) coding for 372 amino acids. The putative ATG initiation codon is preceded by a purine (G) residue in position −3, and by several upstream STOP codons, suggesting that it represents the authentic initiation codon. At the end of the 3' UTR (untranslated region), we found a canonical polyadenylation signal (AATAAA) shortly before the poly A itself. The phosphatase 2C domain of the novel protein, which we named PN7740, is from amino acids 104 to 339 Thus, we have identified a novel phosphatase that binds to the first PTB domain of Fe65. This is very important because the balance of β-secretion vs α-secretion of APP is regulated by phosphorylation (Farber et al., 1995; Caporaso et al., 1992; Buxbaum et al., 1990; Buxbaum et al., 1993; Sabo et al., 1999). We suggest that this balance can be modified by the pharmacological modulation of the interaction between Fe65 and the novel phosphatase, or by the direct pharmacological modulation of the activity the novel phosphatase itself. It is also possible that this novel phosphatase modulates the phosphorylation status of proteins involved in APP metabolism, such as PS1, PS2, and nicastrin. We have submitted the nucleotide and aminoacid sequences of the PN7740 cDMA and protein in a separate patent application. These sequences are added in the appendix of the present application for reference.

The Mint1 protein (also called X11 alpha) is a cytosolic protein that interacts that the C-terminal fragment of APP. Mint1 contains a PTB domain and a PDZ domain. Interaction of Mint1 with APP increases the levels of cellular APP and reduces the levels of both α- and β-secreted forms of APP (Borg et al., 1998b). The mechanism by which Mint1 affects APP metabolism is not clear at this point. Using a fragment of Mint1 from amino acids 447 to 758 as a bait in a yeast two-hybrid search, we found a clone encoding amino acids 364 to 589 of KIAA0427 as a prey. The KDRI (Kazusa DNA Research Institute) database reports the sequence of a full-length clone for this protein, coding for 598 aa. No well characterized protein domain was identified in KIAA0427 and thus its function is unknown. Therefore, for all practical purpose, we consider this protein as functionally novel, although its sequence is not new. The mRNA for KIAA0427 is found at very high levels message in brain, medium levels in lung, kidney, prostate, testis, and ovary, and low levels in all other tissues examined. We suggest that KIAA0427 mediates the effect of Mint1 on APP metabolism and that pharmacological modulation of the Mint1-KIAA0427 interaction might influence APP secretion.

Additional evidence for the role of Mint1 in APP metabolism comes from its interaction with PS1. Using a fragment of PS1 from amino acids 1 to 91 as a bait in a yeast two-hybrid search, we found a clone encoding amino acids 470 to 821 of Mint1 as a prey. This domain contains most of the PTB domain (amino acids 457 to 643) which is known to bind the cytoplasmic domain of APP. Thus, PS1 and APP might compete for the PTB domain of Mint1 and FAD associated mutations in PS1 are expected to alter its interaction with Mint1. We suggest pharmacological modulation of the PS1-Mint1 interaction might influence APP metabolism and amyloid production.

Using a fragment of Mint1 from amino acids 739 to 857 as a bait in a yeast two-hybrid search, we found a clone encoding amino acids 45 to 212 of glutamine synthetase as a prey (GS, also called glutamate ammonia ligase). This enzyme catalyzes the ATP-dependent conversion of L-glutamate and NH3 to glutamine. In the brain, GS is secreted by astrocytes and plays a crucial role in the clearance of excitotoxic glutamate released in synapses. GS concentration is dramatically increased in the CSF from AD patients (Gunnersen and Haley, 1992). This phenomenon could be a defense mechanism against glutamate excitotoxicity, reflecting astrogliosis rather than an Alzheimer specific phenomenon. It is striking that the Aβ peptide interacts with GS and inhibits its activity by oxidative modification (Aksenov et al., 1997). Thus, the inactivation of GS by Aβ could lead to elevated concentration of excitotoxic glutamate. Furthermore, a previous study by the same group (Aksenov et al., 1996) showed that Aβ-mediated inactivation of GS is accompanied by the loss of immunoreactive GS and a concomitant significant increase of Aβ neurotoxicity. The interaction between GS and Mint1 suggests that Mint1 may act as an adapter molecule, bringing GS into a complex with APP. It is thus possible that Mint1 favors the oxidation of GS by Aβ, with the concomitant elevation in synaptic glutamate concentration. We suggest that pharmacological modulation of the Mint1-GS interaction could reduce its oxidation by Aβ and thus keep glutamate concentration below toxic levels.

CASK is a postsynaptic protein of the MAGUK family, which contains a PDZ domain, an SH3 domain, a guanylate kinase domain, and a calmodulin-binding domain. It interacts with Mint1, with APP, and with the neurexins (Borg et al., 1998a; Borg et al., 1999). Using a fragment of CASK from amino acids 306 to 574 as a bait in a yeast two-hybrid search (calmodulin-binding domain and its PDZ domain), we found a clone encoding amino acids 909 to 1280 of dystrophin as a prey. This protein is largely known for its involvement in Duchenne muscular dystrophy (Hoffman, 1999), and was recently localized in post-synaptic densities in rat brain (Kim et al., 1992). Reciprocally, PSD-95 and DLG2 (PSD-93) (Rafael et al., 1998) as well as APP (Askanas et al., 1992) are also found at neuromuscular junctions, where they participate in the clustering of nicotinic acetylcholine receptors, a phenomenon that also requires dystrophin (Kong and Anderson, 1999). The interaction of dystrophin with CASK, together with its localization in brain post-synaptic densities suggest that this protein (and most probably proteins from the dystrophin associated complex, like syntrophin) is another component of the synaptic cytoskeletal structure. Interestingly, both APP and dystrophin are found (often with gelsolin) in the pathological features of several neuromuscular diseases (De Bleecker et al., 1996; Nonaka, 1994). We suggest that adequate pharmacological modulation of the CASK-dystrophin interaction might help prevent the brain or neuromuscular synaptic degeneration observed in many neuropathological conditions.

CIB is a calcium-binding protein that we found to interact with FKBP25, which is itself a PS1 interactor (see U.S. patent application Ser. No. 09/466,139; International Patent Application No. PCT/U.S. 99/30396 (WO 00/37483)). Based on its sequence similarity with calcineurin B, CIB was proposed to be the regulatory subunit of a yet-to-be-discovered calcium-activated phosphatase (Naik et al., 1997). In our previous patent application, we have suggested that this novel putative phosphatase might control the activity of the ryanodine receptor, and thus calcium homeostasis. Recently CIB was found to also interact with PS2 and PS1 (Stabler et al., 1999). Because of the causal role of PS1 and PS2 mutations in Alzheimer's disease, proteins that interact with CIB are likely to play a major role in AD pathogenesis. Mint2 (also called X11 beta) is a cytosolic protein that interacts that the C-terminal fragment of APP (Tomita et al., 1999). Mint2 contains a PTB domain and two PDZ domains. In addition to the cytosolic fragment of APP, Mint1 and Mint2 both bind Munc-18 and are involved in the fusion of synaptic vesicles with the presynaptic membrane (Okamoto and Sudhof, 1997; Okamoto and Sudhof, 1998). Thus, the Mints proteins play a role in APP trafficking and synaptic function. Proteins that associate with the Mints are therefore likely to be involved in AD pathogenesis. Moreover, proteins that associate with CIB and with Mint1 or Mint2 are even more likely to play a central role in AD development. Thus, we used CIB and the Mints proteins as a bait in a yeast two-hybrid search, and we found a prey protein, S1P, that binds to CIB and Mint2.

S1P is a transmembrane protease that catalyzes the first cleavage step of the SREBPs (sterol regulatory element-binding proteins) processing (Sakai et al., 1998). SREBPs are membrane-bound transcription factors that activate genes for enzymes involved in cholesterol and fatty acids biosynthesis (Brown and Goldstein, 1999). Two sequential cleavage steps are necessary to release the active N-terminal domain of SREBPs from endoplasmic reticulum (ER) membranes and for the subsequent targeting of this protein domain to the nucleus. The first step is catalyzed by a protein called S1P (Site 1 Protease) which cleaves SREBPs in the ER luminal domain, while the second step is catalyzed by S2P (Site 2 Protease) which cleaves SREBPs in the first transmembrane domain (Rawson et al., 1997; Ye et al.2000).

This process is controlled by the SREBP cleavage-activating protein (SCAP), a large regulatory protein with eight transmembrane domains that acts as a sterol sensor and is necessary for the activation of the S1P protease (Nohturfft et al., 1999). This protein is also known as SKI-1. In addition to SREBPs, S1P/SKI-1 also cleaves the proBDNF molecule into its active form (Seidah et al., 1999b), and belongs to the subtilisin/kexin family of precursor convertases (Seidah et al., 1999a). Because CIB interacts with both PS1 and PS2, and because Mint2 interacts with APP, S1P might be involved in APP processing. It appears unlikely that S1P is the γ-secretase (since it does not cleave in the transmembrane domain but in the luminal domain), and there is now mounting evidence that PS1 could be the γ-secretase (Wolfe et al., 1999b; Selkoe and Wolfe, 2000; Li et al., 2000a; Li et al., 2000b), although this is still controversial (Murphy et al., 2000; Murphy et al., 1999). Recently, two novel enzymes with β-secretase activity have been identified as BACE and BACE-like (Vassar et al., 1999; Hussain et al., 1999; Yan et al., 1999). It is thus unlikely that S1P represent yet a third enzyme with β-secretase activity. However, we favor the possibility that S1P might be an β-secretase. Although the exact site of APP α-cleavage is immediately after the Lys16 residue of the Aβ peptide (Anderson et al., 1991), mutational analyses have shown that α-secretase has poor sequence specificity (substitution of Lys16 by a Gly, Leu, Thr, Arg, or Met residue did not affect cleavage) (Sisodia, 1992) but cleaves at a distance about 12 to 13 residues away from the membrane. Interestingly, the cleavage of SREBP2 by S1P occurs immediately after the Leu522 residue, which is 12 residues before the second transmembrane domain (Duncan et al., 1997). Additionally, it is also remarkable that S1P activity regulates (and is regulated by) cholesterol levels (Brown and Goldstein, 1999). Raised cholesterol levels reduce the α-secretion of APP (Bodovitz and Klein, 1996). Conceivably, high cholesterol levels could lower S1P activity, thus reducing APP α-secretion. In brief, we have identified a transmembrane protease, S1P, that interacts with CIB and Mint2, that might be involved in APP metabolism, and that shows several important features expected from a putative α-secretase. We suggest that adequate pharmacological modulation of S1P activity or interaction with CIB or Mint2 might shift the metabolism of APP toward the α-secretase pathway.

There is a growing body of evidence that disruption of energy metabolism is an important factor in neurodegenerative disorders, including Alzheimer's Disease (Beal, 1998; Nagy et al., 1999; Rapoport et al., 1996). Mitochondrial dysfunctions result in low ATP levels and production of free oxiradicals that are extremely toxic to neurons (Simonian and Coyle, 1996; Beal, 1996). In Alzheimer's, FAD mutations in PS1 have been shown to trigger neuronal apoptosis through a mechanism involving the disruption of mitochondrial function, energy metabolism, and calcium homeostasis (Guo et al., 1998a; Guo et al., 1999a; Mattson et al., 2000; Begley et al., 1999). To gain further insight into the involvement of mitochondrial function and energy metabolism in AD pathogenesis, we used the presenilins (PS1 and PS2) as well as their common interactor CIB (Stabler et al., 1999) as baits in yeast two-hybrid searches and looked for interactors that are either mitochondrial proteins, or that are involved in energy metabolism. We found an interaction between PS-1 and α-enolase, a glycolytic enzyme which transforms 2-phosphoglycerate into phosphoenol pyruvate, and is thus directly involved in energy production (see U.S. patent application Ser. No. 09/466,139; International Patent Application No. PCT/U.S. 99/30396 (WO 00/37483)).

In addition, we found an interaction between PS1 and phosphoglycerate dehydrogenase (P-glycerate DH). This enzyme is responsible for the oxidation of 3-phosphoglycerate, a glycolysis intermediate, to 3-phosphohydroxypyruvate, an intermediate of the serine biosynthetic pathway. We also found that both PS1 and PS2 interact with glyceraldehyde-3-phosphate dehydrogenase (GAPDH). This enzyme catalyzes the oxidation of glyceraldehyde-3-phosphate to 1,3-diphosphoglycerate, with the concomitant reduction of NAD+ to NADH. In addition to its role in glycolysis, GAPDH is also directly involved in neuronal apoptosis (Chen et al., 1999) and its role in AD pathogenesis is strengthened by its interaction with the cytosolic domain of APP (Schulze et al., 1993). In brief, GAPDH is a central molecule that interacts with all three major Alzheimer proteins (PS1, PS2, and APP), mediates neuronal apoptosis, and is involved in energy metabolism.

We also found that PS1 interacts with the beta subunit of the electron transfer flavoprotein (beta-ETF). This protein is an electron acceptor for several dehydrogenases and transfers electrons to the main respiratory electron transport chain. A disruption of the interaction between PS1 and the electron transfer flavoprotein (possibly caused by FAD mutations) might alter normal mitochondrial function and energy production and thus threaten neuronal survival. We also found an interaction between CIB and the beta subunit of ATP synthase. CIB is a calcium-binding protein that interacts with both PS1 and PS2 (Stabler et al., 1999), and with FKBP25, another PS1 interactor that might also be involved in the regulation of calcium homeostasis (see U.S. patent application Ser. No. 09/466,139; International Patent Application No. /U.S. 99/30396, (WO 00/37483)). These five interactions reported here link PS1, PS2, and CIB to proteins involved in mitochondrial function and energy metabolism, two cellular processes that are severely affected in Alzheimer's and other neurodegenerative diseases. We suggest that adequate pharmacological modulation of these interactions or modulation of the enzymatic activities of the identified preys might prevent the neuronal degeneration observed in AD.

Intracellular calcium is stored mainly inside the endoplasmic reticulum (ER), and is released into the cytosol upon activation of the ryanodine receptor or the inositol-triphosphate (IP3) receptor, two ER transmembrane proteins. The fine regulation of the activity of these two receptors is crucial for the control of calcium homeostasis, and thus for neuronal survival (Mattson and Furukawa, 1996). A number of studies suggest that disruption of calcium homeostasis underlies Aβ neurotoxicity (Mattson, 1994; Joseph and Han, 1992; Mattson et al., 1993a; Guo et al., 1998b). In addition to their role in the production of Aβ42, the presenilins are also known to participate in the control of calcium homeostasis through the regulation of calcium release from internal stores (Mattson et al., 1998; Mattson et al., 1999). Alzheimer associated mutations in the presenilins have been shown to disrupt this control, leading to neuronal apoptosis (Guo et al., 1998b; Guo et al., 1996). PS1 was shown to interact with δ-catenin (Guo et al., 1998b; Guo et al., 1996), but the functional significance of this interaction has remained elusive. We have found that δ-catenin interacts with KIAA0443, a protein that contains a lipocalin domain and is thus probably involved in the transport of small lipophilic molecules (U.S. patent application Ser. No. 09/466,139; International Patent Application No. PCT/U.S. 99/30396 (WO 00/37483)).

Using KIAA0443 as a bait in a yeast two-hybrid search, we found the enzyme phosphatidylinositol-4 kinase (PI-4 kinase) as a prey. This enzyme catalyzes the first commited step in the biosynthesis of IP3. It was reported to be expressed mainly in brain and placenta (Wong and Cantley, 1994). It contains several biologically active domains, including an ankyrin repeat domain, a lipid kinase unique domain, a pleckstrin homology domain, a presumed lipid kinase/protein kinase homology domain, a proline-rich region, and an SH3 domain (Nakagawa et al., 1996). The interaction of KIAA0443 with PI-4 kinase and the presence of a lipocalin domain in KIAA0443 suggest that KIAA0443 might bring a lipid such as phosphatidylninositol in close proximity of the kinase that phosphorylates it. The regulation of this process, leading to the formation of IP3, is obviously important for the control of calcium homeostasis. Because KIAA0443 interacts with δ-catenin, itself a PS 1 interactor, it is possible that PS1 mutations associated with Alzheimer's disrupt the interaction network that includes PSI, δ-catenin, KII-AA0443, and PI-4 kinase. This in turn could lead to an alteration of PI-4 kinase activity, resulting in abnormal levels of IP3 and disruption of calcium homeostasis. We suggest that pharmacological modulation of PI-4 kinase activity or modulation of the protein—protein interactions connecting this enzyme with PSI (via KIAA0443 and δ-catenin) might prevent the disruption of calcium homeostasis and the resulting neuronal apoptosis.

In the same search with KIAA0443 as a bait, we found the serotonin receptor 2A (5HT-2AR) as a prey. Interestingly, the 5HT-2A and 5HT-2C receptors stimulate APP α-secretion, thus precluding Aβ formation (Nitsch et al., 1996). Moreover, the serotonin derivative N-acetylserotonin and melatonin were shown to improve cognition and protect neurons from Aβ toxicity (Bachurin et al., 1999). These findings suggest that 5HT-2AR agonists might prevent amyloid formation as well as protect neurons from Aβ peptide already present. KIAA0443 appears to link the δ-catenin network (which includes the presenilins) to the serotoninergic system, thus opening a novel promising therapeutic avenue. We suggest that pharmacological modulation of the 5HT-2AR and its interaction with KIAA0443 might prevent amyloid formation and might protect neurons from Aβ toxicity.

We previously reported an interaction between APP and KIAA0351, and we suggested that this protein might mediate the neurotrophic effects of APP through its pleckstrin homology (PH) domain and a connection to guanine nucleotide exchange factors (GEFs) and cyclic GMP (see U.S. patent application Ser. No. 09/466,139; International Patent Application No. PCT/U.S. 99/30396 (WO 00/37483)). Using KIAA0351 as a bait in a yeast two-hybrid search, we found the TRIO protein as a prey. TRIO, initially identified as an interactor for LAR, a transmembrane receptor with tyrosine phosphatase activity (Debant et al., 1996), is a large protein (2861 aa) which contains two pleckstrin homology (PH) domains, one SH3 domain, and a protein kinase domain. All these functional domains are clustered in the C-terminal half of the protein. Additionally, TRIO contains two guanine nucleotide exchange factor (GEF) domains; one is rac-specific, and the other one rho-specific (Debant et al., 1996). TRIO contains an Ig-like domain (close to the kinase domain in the C-terminal region), and 4 spectrin repeats (in the N-terminal region).

Thus, APP interacts directly with a transmembrane receptor tyrosine phosphatase, PTPZ (see U.S. patent application Ser. No. 09/466,139; International Patent Application No. PCT/U.S. 99/30396 (WO 00/37483)), and indirectly (through the KIAA0351 and TRIO connection) with another transmembrane receptor tyrosine phosphatase, LAR. The neurotrophic and neuroprotective effects of sAPP are well documented (Jin and Saitoh, 1995; Mattson, 1997a; Saitoh et al., 1995; Mattson et al., 1999; Mattson and Duan, 1999). In this respect, it is important to note that Abl, TRIO, LAR, and other associated proteins are involved in axonal development (Lanier and Gertler, 2000). A more recent study also showed that downregulation of LAR activity prevents apoptosis and increases NGF-induced neurite outgrowth (Yeo et al., 1997). Together with the recent observation that pleiotrophin binding to PTPZ inhibits its activity (Meng et al., 2000), these results suggest that inhibition of receptor tyrosine phosphatase activity is a key element underlying the neurotrophic or neuroprotective effects of secreted factors such as sAPP. We suggest that pharmacological modulation of LAR activity, or modulation of its interaction with TRIO, or modulation of the TRIO interaction with KIAA0351 might potentiate the neuroprotective effect of sAPP.

As described above and in U.S. patent application Ser. No. 09/466,139; International Patent Application No. PCT/U.S. 99/30396 (WO 00/37483), CIB is a calcium-binding protein that we found to interact with FKBP25, which is itself a PS1 interactor (see U.S. patent application Ser. No. 09/466,139; International Patent Application No. PCT/U.S. 99/30396 (WO 00/37483)). Based on its sequence similarity with calcineurin B, CIB was proposed to be the regulatory subunit of a yet-to-be-discovered calcium-activated phosphatase (Naik et al., 1997). We have suggested that this novel putative phosphatase might control the activity of the ryanodine receptor, and thus calcium homeostasis (see We U.S. patent application Ser. No. 09/466,139; International Patent Application No. PCT/U.S. 99/30396 (WO 00/37483)). Recently CIB was found to also interact with PS2 and PS1 (Stabler et al., 1999). Because of the causal role of PS1 and PS2 mutations in Alzheimer's disease, proteins that interact with CIB are likely to play a major role in AD pathogenesis. Using CIB as a bait in a yeast two-hybrid search, we found the mixed lineage kinase 2 (MLK2) as a prey.

MLK2 was originally cloned from human epithelial tumors and described as protein kinases containing two leucine/isoleucine-zipper domains (Dorow et al., 1993). In another study, MLK2 is called MST and described as a kinase of 953 aa, with an SH3 domain, 2 leucine zipper domains, and a proline-rich domain (Katoh et al., 1995). Northern blot data showed that the gene is mostly expressed in brain, skeletal muscle, and testis as a 3.8-kb mRNA. MLK2 belongs to the MAP kinase family and is also called MAP3K10. Interestingly, MLK2-mediated signaling is activated by polyglutamine-expanded huntingtin, the pathogenic form of the protein found in Huntington's disease (Liu et al., 2000). Thus, MLK2 appears to mediate neuronal toxicity in some particular condition. Because it interacts with CIB, it is possible that mutations in the presenilins also activate MLK2, resulting in accelerated neuronal apoptosis, as observed in Alzheimer's. We suggest that pharmacological modulation of MLK2 activity or its interaction with CIB might prevent neuronal death.

BAX is a protein of the Bcl-2 family which mediates apoptosis. Elevated BAX concentrations in the brains of AD patients suggested that BAX might be responsible for the neuronal death observed in AD (Su et al., 1997). Using BAX as a bait in a yeast two-hybrid search, we found the alpha (pore-forming) subunit of the slo ($K^+$ activated) potassium channel. Potassium channels (K channels) are very diverse in structure and function (Jan and Jan, 1997; Christie, 1995). The slo channel (its name comes from the fly slowpoke K channel) is a member of the subfamily of large-conductance calcium activated potassium channels (also called Maxi K or BK or KCa) which belong to the voltage gated K channel (Kv) family. The BK family contains many splice variants, all of which have the typical structure of Kv channels: the alpha subunit is a homotetrameric complex formed by 4 polypeptides, each of which contains 6 transmembrane (TM) domains and often large cytosolic N-terminal and C-terminal domains. The channel (pore) region is between TM5 and TM6, while TM4 acts as a voltage sensor, and calcium binding sites are found in the C-terminal cytosolic domain. Tetraethylammonium (TEA) blocks the activity of these channels (Jan and Jan, 1997; Christie, 1995). A dysfunction of a large conductance TEA-sensitive K channel was identified in fibroblast from AD patients (Etcheberrigaray et al., 1993). Recently, the same channels were found to be activated in response to sAPP, resulting in shut down of neuronal activity and protection against a variety of insults including Ab toxicity (Furukawa et al., 1996a; Goodman and Mattson, 1996). Thus, our finding shows that BAX, a mediator of apoptosis, interacts with the slo K channel, which is involved in the neuroprotective effect of sAPP, and whose activity if disrupted in AD fibroblasts. We suggest that pharmacological modulation of the slo K channel activity of modulation of its interaction with BAX might prevent neuronal apoptosis.

We reported an interaction between δ-catenin and the focal adhesion kinase 2 (FAK2), also called proline-rich tyrosine kinase β(PYKβ) or cell adhesion kinase β (CAKβ) (see U.S. patent application Ser. No. 09/466,139; International Patent Application No. PCT/U.S. 99/30396 (WO 00/37483)). Focal adhesion kinases (FAKs) form a special subfamily of cytoplasmic protein tyrosine kinases (PTKs). In contrast to other non-receptor PTKs, FAKs do not contain SH2 or SH3 domains, but have a carboxy-terminal proline-rich domain which is important for protein—protein interactions (Schaller, 1997; Schaller and Parsons, 1994; Parsons et al., 1994). FAK2 is expressed at highest levels in brain, at medium levels in kidney, lung, and thymus, and at low levels in spleen and lymphocytes (Avraham et al., 1995). In brain, FAK2 is found at highest levels in the hippocampus and amygdala (Avraham et al., 1995), two areas severely affected in Alzheimer's disease. FAK2 is thought to participate in signal transduction mechanisms elicited by cell-to-cell contacts (Sasaki et al., 1995). It is involved in the calcium-induced regulation of ion channels, and it is activated by the elevation of intracellular calcium concentration following the activation of G protein-coupled receptors (GPCRs) that signal though Gαq and the phospholipase C (PLC) pathway (Yu et al., 1996). Thus, FAK2 is an important intermediate signaling molecule between GPCRs activated by neuropeptides or neurotransmitters and downstream signals that modulate the neuronal activity (channel activation, membrane depolarization). Such a link between intracellular calcium levels, tyrosine phosphorylation, and neuronal activity is clearly important for neuronal survival and synaptic plasticity (Siciliano et al., 1996). The interaction of FAK2 with δ-catenin and its high levels of expression in hippocampus and amygdala suggest that a disruption of its activity may be related to neuronal death in AD.

To gain more insight into the mechanism by which FAK2 mediates neuronal functions and survival, we used FAK2 as a bait in a yeast two hybrid searches. One of the preys identified was SUR1, the type-1 sulfonylurea receptor. Two types of sulfonylurea receptors, SUR1 and SUR2, constitute the regulatory unit of ATP-sensitive inward rectifying potassium channels ($K_{ATP}$ channels), while the channel-forming unit belongs to the Kir6.x family (Bryan and Aguilar-Bryan, 1999; Inagaki and Seino, 1998). A major role of these channels is to link the metabolic state of the cell to its membrane potential: $K_{ATP}$ channels close upon binding intracellular ATP to depolarize the cell and open when ATP concentrations return to resting levels. These channels are involved in events such as insulin secretion from pancreatic b cells, ischemia responses in cardiac and cerebral tissues, and regulation of vascular smooth muscle tone (Inagaki et al., 1995; Ashcroft and Ashcroft, 1992). The activity of these channels in pancreatic b cells, where they play a crucial role in the secretion of insulin, has been extensively studied: following an elevation of blood glucose levels, the intracellular concentration of ATP in pancreatic b cells rises, resulting in channel closure and cell depolarization. This allows $Ca^{2+}$ ions to enter the cell through voltage-sensitive $Ca^{2+}$ channels, which will trigger the fusion of insulin secretory vesicles with the plasma membrane and release of insulin (Satin, 1996; Ashcroft, 1996). In neurons, the same mechanisms involving $K_{ATP}$ channels (linking the metabolic state of the cell to its membrane potential) control neurotransmitter release.

We also reported an interaction between acetylcholinesterase and α-endosulfine, an endogenous ligand for SUR1 (Virsolvy-Vergine et al., 1992) (see, U.S. patent application Ser. No. 09/466,139; International Patent Application No. PCT/U.S. 99/30396 (WO 00/37483)). Because of its role in pancreatic beta cells, where is stimulates insulin secretion (Heron et al., 1998), we suggested that in the brain, endosulfine binding to the sulfonylurea receptor would also shut down $K_{ATP}$ channels, leading to depolarization, $Ca^{2+}$ entry, vesicle fusion, and release of the vesicular content into the synaptic cleft. While the activity of $K_{ATP}$ channels is down-regulated by ATP binding to the SUR subunit, phosphorylation of the Kir6.x subunit by PKA stimulates channel activity (Lin et al., 2000). Interestingly, endosulfine is also a PKA substrate (Virsolvy-Vergine et al., 1992; Heron et al., 1998; Heron et al., 1999). The interaction of SUR1 with FAK2 suggests that additional phosphorylation events (of any of the channel subunit) might control channel activity. $K_{ATP}$ channels are very amenable to pharmacological modulation and drugs that active ($K^+$ channels openers (PCO) such as diazoxide and cromakalim) or inhibit the channels ($K^+$ channels blockers (PCB) such as the sulfonylureas glibenclamide and tolbutamide) have been identified (Lawson, 1996a; Lawson, 1996b). The function of $K_{ATP}$ channels in the brain is under intense investigation, and the expression of different $K_{ATP}$ channels in the hippocampus (Zawar et al., 1999) opens a therapeutic opportunity against hippocampal neurodegeneration. In fact, the PCO cromakalim was shown to protect neurons in the hippocampus from glutamate toxicity through a mechanism closely related to the control of calcium homeostasis (Lauritzen et al., 1997). Another study recently showed that $K_{ATP}$ channels are neuroprotective against the effects cellular stress caused by energy depletion (Lin et al., 2000). Both calcium homeostasis and energy metabolism are crucial cellular functions that are very affected in neurodegenerative diseases such as AD. We suggest that pharmacological modulation of brain K channels containing SUR1, or modulation of the interaction between SUR1 and FAK2, might help prevent the neuronal loss observed in the brain of AD patients.

Cyclic GMP (cGMP) is a small molecule involved in a number of cellular functions that relate to neuronal survival or death. There is evidence that intracellular cGMP mediates some of the neurotrophic effects of sAPP (Barger et al., 1995), as well as the neuroprotective action of somatostatin (Forloni et al., 1997). However, there is also evidence that intracellular cGMP is neurotoxic while extracellular cGMP is neuroprotective (Montoliu et al., 1999). Recently, Chalimoniuk and Strosznajder looked at the effects of aging and the Ab peptide on nitric oxide (NO) and cGMP signaling in the hippocampus (Chalimoniuk and Strosznajder, 1998). They showed that aging coincided with a decrease in the basal level of cGMP as a consequence of a more active degradation of cGMP by a phosphodiesterase in the aged brain as compared to the adult brain. Moreover, a loss of the NMDA receptor-stimulated enhancement of the cGMP level determined in the presence of cGMP-phosphodiesterase inhibitor 3-isobutyl-1-methylxanthine was observed in hippocampus and cerebellum of aged rats. The neurotoxic Ab25-35 peptide decreased significantly the NMDA receptor-mediated calcium, and calmodulim-dependent NO synthesis that may then be responsible for disturbances of the NO and cGMP signaling pathway. They concluded that cGMP-dependent signal transduction in hippocampus and cerebellum may become insufficient in senescent brain and may have functional consequences in disturbances of learning and memory processes, and that the Ab peptide may be an important factor in decreasing the NO-dependent signal transduction mediated by NMDA receptors resulting in decreased cGMP levels. Thus, the effects of cGMP are quite complex and branch into other pathways such as nitric oxide (NO), NMDA receptor, and calcium homeostasis. The growing evidence for a neuroprotective effect of cGMP (Barger et al., 1995; Forloni et al., 1997; Chalimoniuk and Strosznajder, 1998) suggests that inhibition of a cGMP-specific phosphodiesterase such as PDE-9A might prove beneficial. Using Mint2 as a bait in a yeast two-hybrid search, we found phosphodiesterase 9A (PDE-9A), a cGMP-specific phosphodiesterase as a prey. The mRNA for PDE-9A was found in all tissues examined, with highest levels in spleen, small intestine, and brain (Fisher et al., 1998). Because PDE-9A interacts directly with a protein from the APP pathway (Mint2), and because cGMP mediates some of the neurotrophic effects of sAPP (Barger et al., 1995), we suggest that pharmacological modulation of PDE-9A activity or its interaction with Mint2 might potentiates the neurotrophic effects of sAPP and prevent neuronal death observed in AD brains.

Using CIB as a bait in a yeast two-hybrid search, we found the stearoyl CoA desaturase (SCD2, also called Delta (9) desaturase) as a prey. This enzyme is a component of the liver microsomal stearoyl-CoA desaturase system that catalyzes the insertion of a double bond into various fatty acyl-CoA substrates. It needs iron as a cofactor and is localized in the endoplasmic reticulum. In the peripheral nervous system, SCD2 is involved in lipid biosynthesis associated with myelinogenesis (Garbay et al., 1998). Its function in brain is less clear, as its expression pattern through development does not coincide well with that of true myelin genes (Garbay et al., 1997). Still, its function in lipid biosynthesis appears to be compatible with a role in myelination. This interaction between CIB and SCD suggests that the metabolic disorder leading to amyloid plaques and tangles formation, neuronal and synaptic loss, could also downregulate SCD2 activity and in turn result in demyelination, as observed in AD brains. Thus, we propose that pharmacological modulation of SCD2 or its interaction with CIB might prevent the myelin loss observed in AD brain and other neurodegenerative conditions.

We described the interaction between PS1 and rab11, a small GTPase involved in the traffic of intracellular vesicles (see U.S. patent application Ser. No. 09/466,139; International Patent Application No. PCT/U.S. 99/30396 (WO 00/37483)). Rab11 is found predominantly in recycling endosomes (Ullrich et al., 1996; Sheff et al., 1999). It also plays a role in the transport of vesicles from the trans-Golgi network to the plasma membrane and in secretory mechanisms in PC12 cells (Urbe et al., 1993; Chen et al., 1998). These observations confirm the role of PS1 in vesicular trafficking. We have used rab11 as a bait in the yeast two-hybrid system and found that it interacts with the focal adhesion kinase (FAK). This protein is a tyrosine kinase found at focal adhesion sites, and which mediates the signals elicited by a variety of hormone and neurotransmitter receptors (Schaller and Parsons, 1994; Parsons et al., 1994; Zachary, 1997; Schlaepfer et al., 1999). These signals are involved in the control of a number of cellular events including cell growth, migration, and survival. In neurons, FAK is also involved in neurite extension (Park et al., 2000). In addition to its role in neuronal survival and synaptic stability (Girault et al., 1999; Tamura et al., 1999), FAK activity is known to be disrupted by the A$\beta$ protein (Zhang et al., 1994; Berg et al., 1997). Thus, we have identified a tyrosine kinase whose activity is important for neuronal survival and function, and which interacts that rab11, a protein involved in vesicular trafficking and which binds to PS1. It is thus possible that FAD mutations in PS1 might alter FAK activity and thus disrupt neuronal function and survival.

To gain more information about the involvement of FAK in neurodegeneration and Alzheimer's disease, we used FAK as a bait in a yeast two-hybrid search and we found casein kinase II (CK2) as a prey. As mentioned above, there is a large body of evidence that phosphorylation cascades are deeply altered in the brain of AD patients (Jin and Saitoh, 1995; Saitoh et al., 1991; Farlow, 1998). Among the numerous kinases that are affected in AD, CK2 levels showed a dramatic overall reduction (84%), although CK2 levels varied a lot between sick (tangle-bearing) neurons and healthy (tangle-free) neurons (Iimoto et al., 1990). In addition, although CK2 is not part of the paired helical filaments (PHF), it is clearly associated with neurofibrillary tangles (Baum et al., 1992). As the CK2 alterations were shown to precede tau accumulation and tangle formation (Masliah et al., 1992), it was suggested that CK2 might play a role in tau hyperphosphorylation (and thus tangle formation). However, the biochemical mechanism whereby CK2 is activated is still unclear. The observation that CK2 is activated in cultured cells treated with insulin, IGF-I, and EGF (Krebs et al., 1988) (factors that signal through tyrosine kinase receptors) suggests that the aberrant CK2 cascade observed in AD could reflect an altered tyrosine phosphorylation balance. Recent studies showed that in turn, CK2 activity can stimulate the tyrosine phosphorylation cascade elicited by the insulin receptor (Marin et al., 1996), and that CK2 itself can have tyrosine kinase activity (Marin et al., 1999). Thus, there is clear evidence for a link between CK2 and tyrosine phosphorylation cascades, and the direct interaction between CK2 and FAK suggests that their respective activities might be coordinately regulated. We suggest that adequate pharmacological modulation of FAK activity or CK2 activity, or the interaction between FAK and rab11 or between FAK and CK2 might prevent neuronal dysfunction and death observed in the brain of Alzheimer's patients and other neurodegenerative conditions.

In the same search, we also identified glutathione-S-transferase M3 as a FAK interactor, further supporting the involvement of FAK in neurodegeneration and Alzheimer's disease. Free radical neurotoxicity (through the generation of lipid peroxidation products) is well documented and was proposed to mediate as least some aspect of A$\beta$ toxicity (Mark et al., 1996; Butterfield, 1997; Whitehouse, 1997), probably through the generation of 4-hydroxynonenal (HNE) (Keller and Mattson, 1998). There is also ample evidence that antioxidant molecules protect neurons, and in particular, glutathione transferase (GST) protects neurons against toxicity induced by HNE (Xie et al., 1998). In this respect, it is interesting that the activity of GST is reduced in AD brain and CSF compared to controls (Lovell et al., 1998). Thus, this interaction between FAK and GST generates a new link between two independent pathways that are involved in neuron survival and that are altered in the brains of Alzheimer patients. We suggest that adequate pharmacological modulation of FAK activity or GST activity, or the interaction between FAK and GST might prevent neuronal dysfunction and death observed in the brain of Alzheimer's patients and other neurodegenerative conditions.

We reported an interaction between $\delta$-catenin and bcr (break point cluster), and we explained the relevance of this interaction in the context of neurodegeneration and Alzheimer's Disease (see U.S. patent application Ser. No. 09/466, 139; International Patent Application No. PCT/U.S. 99/30396 (WO 00/37483)). In subsequent experiments, we have used bcr itself has a bait in yeast two-hybrid searches, and have found a number of interactions, reported here, that strengthen our initial claim that the bcr protein plays an important role in the brain. Using a C-terminal bait of bcr (aa 1206 to 1271) in a yeast two-hybrid search, we found the neuroendocrine protein Discs Large 3 (NE-dlg, or DLG3), also known as SAP102 (synapse-associated protein 102), and the postsynaptic density protein PSD95 (DLG4), also known as SAP90. These two proteins are 67% identical (81% similar) to each other, and both function as synaptic scaffolding proteins that interact with synaptic receptors and associated molecules. PSD95 interacts with the NMDA receptor (Kornau et al., 1995) and this interaction is altered by transient global ischemia (Takagi et al., 2000). Nitric oxide synthase (NOS), an enzyme that regulates the activity of the NMDA receptor, also interacts with PSD95, and this interaction is displaced by CAPON (Jaffrey et al., 1998). DLG3 also interacts with the NMDA receptor (Lau et al., 1996; Muller et al., 1996). The well documented role of the NMDA receptor in long-term potentiation (LTP) in the hippocampus (Muller et al., 1995; Sans et al., 2000) suggests that proteins such as PSD95 and DLG3 play important synaptic functions underlying learning and memory. In addition, PSD95 also interacts with several types of potassium channels (Laube et al., 1996; Nehring et al., 2000). The activity of those channels is clearly involved in neuronal survival (Holm et al., 1997; Mattson, 1997a), particularly in the hippocampus (Zawar and Neumcke, 2000). Thus, through it clustering function of potassium channels, PSD95 also plays a role in neuronal survival.

It is also interesting to note that PSD95 interacts with SynGAP (Kim et al., 1998), an activating protein for the GTPase Ras. Thus, PSD95 interacts with at least two proteins that activate GTPases: SynGAP and bcr (Braselmann and McCormick, 1995; Diekmann et al., 1995). Using the same C-terminal bait of bcr (aa 1206 to 1271) in a yeast two-hybrid search, we also found the transcription factor HTF4A as an interactor. HTF4A is a protein of 682 amino acids, from the myc family of basic helix-loop-helix (bHLH) transcription factors. HTF4A activates the transcription of a number of genes by binding to E-box motifs, including the gene for the al acetylcholine receptor (AChR) (Neville et al., 1998). HTF4A also stimulates the transcription of the vgf gene (Di Rocco et al., 1997), a secreted neuropeptide whose expression is induced by several neurotrophins (Snyder et al., 1998). Decreased levels of vgf mRNA in the hippocampus have been correlated with age-induced cognitive decline in rats (Sugaya et al., 1998). Thus, reduced HTF4A-dependent transcriptional activity in the hippocampus could be associated with age-related memory loss. This interaction strengthens the finding that bcr and associated proteins play an important synaptic function in the hippocampus.

Using a bcr bait from aa 856 to 1226 in a yeast two-hybrid search, we found a novel human protein as an interactor. This novel protein is 94% identical to mouse semaphorin F (M-sema F). The semaphorins belong to a family of secreted and membrane bound proteins involved in the nervous system development and axonal guidance. Semaphorin F is a transmembrane form (Inagaki et al., 1995). Recently, the cytosolic C-terminal domain of M-sema F was found to interact with GIPC (also named Semcap1) (Wang et al., 1999). Thus, semaphorin F is a common interactor to bcr and GIPC, as is δ-catenin. Using a C-terminal bait of bcr (aa 1206 to 1271) in a yeast two-hybrid search, we also found SRCAP (Snf2-related CBP activator protein) as an interactor. This finding further support the involvement of bcr in hippocampal synaptic function. CBP (CREB-binding protein) is a co-activator for a number of transcription factors and interacts with a number of proteins such as histone acetyltransferases, general transcription factors, and other co-activators.

Recently, a novel CBP-interacting protein was identified and named SRCAP (Johnston et al., 1999). This protein has ATPase activity and activates transcription of several genes. Because bcr interacts with proteins such as δ-catenin, PSD95, Semaphorin F, and DLG3 (all involved in synaptic function), and because CREB-mediated immediate early transcription is essential for LTP in the hippocampus (Walton et al., 1999), this interaction between bcr and SRCAP brings together the essential components of hippocampal synaptic modulation. Because bcr was found as an interactor with δ-catenin (see U.S. patent application Ser. No. 09/466,139; International Patent Application No. PCT/U.S. 99/30396 (WO 00/37483)), the interactions reported in the present application (bcr with PSD95, DLG3, Semaphorin F, HTF4A, and SRCAP) generate a pathway that links δ-catenin and to synaptic functions and neuronal survival. We suggest that adequate pharmacological modulation the interactions between bcr and any of the five bcr interactors described here might prevent synaptic dysfunction and neuronal death observed in the brain of Alzheimer's patients and other neurodegenerative conditions.

We report interactions between PSD95 and the novel protein PN7740. PSD95 is a member of the MAGUK family (membrane associated guanylate kinase) and contains three PDZ domains, one SH3 domain, and one guanylate kinase (GK) domain (Wheal et al., 1998; Dimitratos et al., 1999). Also called DLG4 and SAP-90 (Kistner et al., 1993; Stathakis et al., 1997), PSD95 is found at the post-synaptic density where it interacts with other synaptic scaffolding proteins and with synaptic signalling proteins such as neurotransmitter receptors and channels (e.g. NMDA receptors, potassium channels) (Kornau et al., 1995; Nagano et al., 1998; Lau et al., 1996; Nehring et al., 2000). PN7740 is a novel protein that we reported as an Fe65 interactor (see above). The full-length cDNA for PN7740 contains a open reading frame (ORF) coding for 372 amino acids. The ID putative ATG initiation codon is preceded by a purine (G) residue in position −3, and by several upstream STOP codons, suggesting that it represents the authentic initiation codon. At the end of the 3' UTR (untranslated region), we found a canonical polyadenylation signal (AATAAA) shortly before the poly A itself. A phosphatase 2C domain was found from amino acids 104 to 339. Thus, we identified a novel phosphatase that binds to the first PTB domain of Fe65.

The proteins disclosed in the present invention were found to interact with PS1, APP or other proteins involved in AD, in the yeast two-hybrid system. Because of the involvement of these proteins in AD, the proteins disclosed herein also participate in the pathogenesis of AD. Therefore, the present invention provides a list of uses of those proteins and DNA encoding those proteins for the development of diagnostic and therapeutic tools against AD. This list includes, but is not limited to, the following examples.

Two-Hybrid System

The principles and methods of the yeast two-hybrid system have been described in detail elsewhere (e.g., Bartel and Fields, 1997; Bartel et al., 1993; Fields and Song, 1989; Chevray and Nathans, 1992). The following is a description of the use of this system to identify proteins that interact with a protein of interest, such as PS 1.

The target protein is expressed in yeast as a fusion to the DNA-binding domain of the yeast Gal4p. DNA encoding the target protein or a fragment of this protein is amplified from cDNA by PCR or prepared from an available clone. The resulting DNA fragment is cloned by ligation or recombination into a DNA-binding domain vector (e.g., pGBT9, pGBT.C, pAS2-1) such that an in-frame fusion between the Gal4p and target protein sequences is created.

The target gene construct is introduced, by transformation, into a haploid yeast strain. A library of activation domain fusions (i.e., adult brain cDNA cloned into an activation domain vector) is introduced, by transformation into a haploid yeast strain of the opposite mating type. The yeast strain that carries the activation domain constructs contains one or more Gal4p-responsive reporter gene(s), whose expression can be monitored. Examples of some yeast reporter strains include Y190, PJ69, and CBY14a. An aliquot of yeast carrying the target gene construct is combined with an aliquot of yeast carrying the activation domain library. The two yeast strains mate to form diploid yeast and are plated on media that selects for expression of one or more Gal4p-responsive reporter genes. Colonies that arise after incubation are selected for further characterization.

The activation domain plasmid is isolated from each colony obtained in the two-hybrid hybrid search. The sequence of the insert in this construct is obtained by the dideoxy nucleotide chain termination method. Sequence information is used to identify the gene/protein encoded by the activation domain insert via analysis of the public nucleotide and protein databases. Interaction of the activation domain fusion with the target protein is confirmed by testing for the specificity of the interaction. The activation domain construct is co-transformed into a yeast reporter strain with either the original target protein construct or a variety of other DNA-binding domain constructs. Expression of the reporter genes in the presence of the target protein but not with other test proteins indicates that the interaction is genuine.

In addition to the yeast two-hybrid system, other genetic methodologies are available for the discovery or detection of protein—protein interactions. For example, a mammalian two-hybrid system is available commercially (Clontech, Inc.) that operates on the same principle as the yeast two-hybrid system. Instead of transforming a yeast reporter strain, plasmids encoding DNA-binding and activation domain fusions are transfected along with an appropriate reporter gene (e.g., lacZ) into a mammalian tissue culture cell line. Because transcription factors such as the *Saccharomyces cerevisiae* Gal4p are functional in a variety of different eukaryotic cell types, it would be expected that a two-hybrid assay could be performed in virtually any cell line of eukaryotic origin (e.g., insect cells (SF9), fungal cells, worm cells, etc.). Other genetic systems for the detection of protein—protein interactions include the so-called SOS recruitment system (Aronheim et al., 1997).

Protein—Protein Interactions

Protein interactions are detected in various systems including the yeast two-hybrid system, affinity chromatography, co-immunoprecipitation, subcellular fractionation and isolation of large molecular complexes. Each of these method is well characterized and can be readily performed by one skilled in the art. See, e.g., U.S. Pat. Nos. 5,622,852 and 5,773,218, and PCT published application Nos. WO 97/27296 and WO 99/65939, each of which are incorporated herein by reference.

The protein of interest can be produced in eukaryotic or prokaryotic systems. A cDNA encoding the desired protein is introduced in an appropriate expression vector and transfected in a host cell (which could be bacteria, yeast cells, insect cells, or mammalian cells). Purification of the expressed protein is achieved by conventional biochemical and immunochemical methods well known to those skilled in the art. The purified protein is then used for affinity chromatography studies: it is immobilized on a matrix and loaded on a column. Extracts from cultured cells or homogenized tissue samples are then loaded on the column in appropriate buffer, and non-binding proteins are eluted. After extensive washing, binding proteins or protein complexes are eluted using various methods such as a gradient of pH or a gradient of salt concentration. Eluted proteins can then be separated by two-dimensional gel electrophoresis, eluted from the gel, and identified by micro-sequencing. The purified proteins can also be used for affinity chromatography to purify interacting proteins disclosed herein. All of these methods are well known to those skilled in the art.

Similarly, both proteins of the complex of interest (or interacting domains thereof) can be produced in eukaryotic or prokaryotic systems. The proteins (or interacting domains) can be under control of separate promoters or can be produced as a fusion protein. The fusion protein may include a peptide linker between the proteins (or interacting domains) which, in one embodiment, serves to promote the interaction of the proteins (or interacting domains). All of these methods are also well known to those skilled in the art.

Purified proteins of interest, individually or a complex, can also be used to generate antibodies in rabbit, mouse, rat, chicken, goat, sheep, pig, guinea pig, bovine, and horse. The methods used for antibody generation and characterization are well known to those skilled in the art. Monoclonal antibodies are also generated by conventional techniques. Single chain antibodies are further produced by conventional techniques.

DNA molecules encoding proteins of interest can be inserted in the appropriate expression vector and used for transfection of eukaryotic cells such as bacteria, yeast, insect cells, or mammalian cells, following methods well known to those skilled in the art. Transfected cells expressing both proteins of interest are then lysed in appropriate conditions, one of the two proteins is immunoprecipitated using a specific antibody, and analyzed by polyacrylamide gel electrophoresis. The presence of the binding protein (co-immunoprecipitated) is detected by immunoblotting using an antibody directed against the other protein. Co-immunoprecipitation is a method well known to those skilled in the art.

Transfected eukaryotic cells or biological tissue samples can be homogenized and fractionated in appropriate conditions that will separate the different cellular components. Typically, cell lysates are run on sucrose gradients, or other materials that will separate cellular components based on size and density. Subcellular fractions are analyzed for the presence of proteins of interest with appropriate antibodies, using immunoblotting or immunoprecipitation methods. These methods are all well known to those skilled in the art.

Disruption of Protein—Protein Interactions

It is conceivable that agents that disrupt protein—protein interactions can be beneficial in AD. Each of the methods described above for the detection of a positive protein—protein interaction can also be used to identify drugs that will disrupt said interaction. As an example, cells transfected with DNAs coding for proteins of interest can be treated with various drugs, and co-immunoprecipitations can be performed. Alternatively, a derivative of the yeast two-hybrid system, called the reverse yeast two-hybrid system (Lenna and Hannink, 1996), can be used, provided that the two proteins interact in the straight yeast two-hybrid system.

Modulation of Protein—Protein Interactions

Since the interactions described herein are involved in the AD pathway, the identification of agents which are capable of modulating the interactions will provide agents which can be used to track AD or to use lead compounds for development of therapeutic agents. An agent may modulate expression of the genes of interacting proteins, thus affecting interaction of the proteins. Alternatively, the agent may modulate the interaction of the proteins. The agent may modulate the interaction of wild-type with wild-type proteins, wild-type with mutant proteins, or mutant with mutant proteins. Agents which may be used to modulate the protein interaction inlcude a peptide, an antibody, a nucleic acid, an antisense compound or a ribozyme. The nucleic acid may encode the antibody or the antisense compound. The peptide may be at least 4 amino acids of the sequence of either of the interacting proteins. Alternatively, the peptide may be from 4 to 30 amino acids (or from 8 to 20 amino acids) that is at least 75% identical to a contiguous span of amino acids of either of the interacting proteins. The peptide may be covalently linked to a transporter capable of increasing cellular uptake of the peptide. Examples of a suitable transporter include penetratins, l-Tat$_{49-57}$, d-Tat$_{49-57}$, retro-inverso isomers of l- or d-Tat$_{49-57}$, L-arginine oligomers, D-arginine oligomers, L-lysine oligomers, D-lysine oligomers, L-histine oligomers, D-histine oligomers, L-ornithine oligomers, D-ornithine oligomers, short peptide sequences derived from fibroblast growth factor, Galparan, and HSV-1 structural protein VP22, and peptoid analogs thereof. Agents can be tested using transfected host cells, cell lines, cell models or animals, such as described herein, by techniques well known to those of ordinary skill in the art, such as disclosed in U.S. Pat. Nos. 5,622,852 and 5,773,218, and PCT published application Nos. WO 97/27296 and WO 99/65939, each of which are incorporated herein by reference. The modulating effect of the agent can be tested in vivo or in vitro. Agents can be provided for testing in a phage display library or a combinatorial library. Exemplary of a method to screen agents is to measure the effect that the agent has on the formation of the protein complex.

Mutation Screening

The proteins disclosed in the present invention interact with one or more proteins known to be involved in AD.

Mutations in interacting proteins could also be involved in the development of AD, for example, through a modification of protein—protein interaction, or a modification of enzymatic activity, modification of receptor activity, or through an unknown mechanism. Therefore, mutations can be found by sequencing the genes for the proteins of interest in patients having the physiological disorder, such as insulin, and non-affected controls. A mutation in these genes, especially in that portion of the gene involved in protein interactions in the physiological pathway, can be used as a diagnostic tool and the mechanistic understanding the mutation provides can help develop a therapeutic tool.

Screening for At-Risk Individuals

Individuals can be screened to identify those at risk by screening for mutations in the protein disclosed herein and identified as described above. Alternatively, individuals can be screened by analyzing the ability of the proteins of said individual disclosed herein to form natural complexes. Further, individuals can be screened by analyzing the levels of the complexes or individual proteins of the complexes or the mRNA encoding the protein members of the complexes. Techniques to detect the formation of complexes, including those described above, are known to those skilled in the art. Techniques and methods to detect mutations are well known to those skilled in the art. Techniques to detect the level of the complexes, proteins or mRNA are well known to those skilled in the art.

Cellular Models of AD

A number of cellular models of AD have been generated and the use of these models is familiar to those skilled in the art. As an example, secretion of the Aβ peptide from cultured cells can be measured with appropriate antibodies. Likewise, the proportion of Aβ40 and Aβ42 can be readily determined. Neuron survival assays and neurite extension assays in the presence of various toxic agents (the Aβ peptide, free radicals, others) are also well known to those skilled in the art. Primary neuronal cultures or established neuronal cell lines can be transfected with expression vectors encoding the proteins of interest, either wild-type proteins or Alzheimer's-associated mutant proteins. The effect of these proteins on parameters relevant to AD (Aβ secretion, neuronal survival, neurite extension, or others) can be readily measured. Furthermore, these cellular systems can be used to screen drugs that will influence those parameters, and thus be potential therapeutic tools in AD. Alternatively, instead of transfecting the DNA encoding the protein of interest, the purified protein of interest can be added to the culture medium of the neurons, and the relevant parameters measured.

Animal Models

The DNA encoding the protein of interest can be used to create animals that overexpress said protein, with wild-type or mutant sequences (such animals are referred to as "transgenic"), or animals which do not express the native gene but express the gene of a second animal (referred to as "transplacement"), or animals that do not express said protein (referred to as "knock-out"). The knock-out animal may be an animal in which the gene is knocked out at a determined time. The generation of transgenic, transplacement and knock-out animals (normal and conditioned) uses methods well known to those skilled in the art.

In these animals, parameters relevant to AD can be measured. These include Aβ secretion in the cerebrospinal fluid, Aβ secretion from primary cultured cells, the neurite extension activity and survival rate of primary cultured cells, concentration of Aβ peptide in homogenates from various brain regions, the presence of neurofibrillary tangles and senile plaques in the brain, the total amyloid load in the brain, the density of synaptic terminals and the neuron counts in the brain. Additionally, behavioral analysis can be performed to measure learning and memory performance of the animals. The tests include, but are not limited to, the Morris water maze and the radial-arm maze. The measurements of biochemical and neuropathological parameters, and of behavioral parameters (learning and memory), are performed using methods well known to those skilled in the art. These transgenic, transplacement and knock-out animals can also be used to screen drugs that may influence these biochemical, neuropathological, and behavioral parameters relevant to AD. Cell lines can also be derived from these animals for use as cellular models of AD, or in drug screening.

Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. Several approaches for use in rational drug design include analysis of three-dimensional structure, alanine scans, molecular modeling and use of anti-id antibodies. These techniques are well known to those skilled in the art. Such techniques may include providing atomic coordinates defining a three-dimensional structure of a protein complex formed by said first polypeptide and said second polypeptide, and designing or selecting compounds capable of interfering with the interaction between a first polypeptide and a second polypeptide based on said atomic coordinates.

Following identification of a substance which modulates or affects polypeptide activity, the substance may be further investigated. Furthermore, it may be manufactured and/or used in preparation, i.e., manufacture or formulation, or a composition such as a medicament, pharmaceutical composition or drug. These may be administered to individuals.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This approach might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

A template molecule is then selected, onto which chemical groups that mimic the pharmacophore can be grafted. The template molecule and the chemical groups grafted thereon can be conveniently selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent it is exhibited. Further optimization or modification can then be carried out to arrive at one or more final mimetics for in vivo or clinical testing.

Diagnostic Assays

The identification of the interactions disclosed herein enables the development of diagnostic assays and kits, which can be used to determine a predisposition to or the existence of a physiological disorder. In one aspect, one of the proteins of the interaction is used to detect the presence of a "normal" second protein (i.e., normal with respect to its ability to interact with the first protein) in a cell extract or a biological fluid, and further, if desired, to detect the quantitative level of the second protein in the extract or biological fluid. The absence of the "normal" second protein would be indicative of a predisposition or existence of the physiological disorder. In a second aspect, an antibody against the protein complex is used to detect the presence and/or quantitative level of the protein complex. The absence of the protein complex would be indicative of a predisposition or existence of the physiological disorder.

Nucleic Acids and Proteins

A nucleic acid or fragment thereof has substantial identity with another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, more preferably at least about 95% of the nucleotide bases, and more preferably at least about 98% of the nucleotide bases. A protein or fragment thereof has substantial identity with another if, optimally aligned, there is an amino acid sequence identity of at least about 30% identity with an entire naturally-occurring protein or a portion thereof, usually at least about 70% identity, more ususally at least about 80% identity, preferably at least about 90% identity, more preferably at least about 95% identity, and most preferably at least about 98% identity.

Identity means the degree of sequence relatedness between two polypeptide or two polynucleotides sequences as determined by the identity of the match between two strings of such sequences. Identity can be readily calculated. While there exist a number of methods to measure identity between two polynucleotide or polypeptide sequences, the term "identity" is well known to skilled artisans (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). Methods commonly employed to determine identity between two sequences include, but are not limited to those disclosed in Guide to Huge Computers, Martin J. Bishop, ed., Academic Press, San Diego, 1994, and Carillo, H., and Lipman, D., *SIAM J Applied Math.* 48:1073 (1988). Preferred methods to determine identity are designed to give the largest match between the two sequences tested. Such methods are codified in computer programs. Preferred computer program methods to determine identity between two sequences include, but are not limited to, GCG (Genetics Computer Group, Madison Wis.) program package (Devereux, J., et al., *Nucleic Acids Research* 12(1).387 (1984)), BLASTP, BLASTN, FASTA (Altschul et al. (1990); Altschul et al. (1997)). The well-known Smith Waterman algorithm may also be used to determine identity.

Alternatively, substantial homology or similarity exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. See, e.g., Asubel, 1992; Wetmur and Davidson, 1968.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

Large amounts of the nucleic acids of the present invention may be produced by (a) replication in a suitable host or transgenic animals or (b) chemical synthesis using techniques well known in the art. Constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate which allow the protein to cross and/or lodge in cell membranes, and thus attain its functional topology, or be secreted from the cell. Such vectors may be prepared by means of standard recombinant techniques well known in the.

The nucleic acid or protein may also be incorporated on a microarray. The preparation and use of microarrays are well known in the art. Generally, the microarray may contain the entire nucleic acid or protein, or it may contain one or more fragments of the nucleic acid or protein. Suitable nucleic acid fragments may include at least 17 nucleotides, at least 21 nucleotides, at least 30 nucleotides or at least 50 nucleotides of the nucleic acid sequence, particularly the coding sequence. Suitable protein fragments may include at least 4 amino acids, at least 8 amino acids, at least 12 amino acids, at least 15 amino acids, at least 17 amino acids or at least 20 amino acids. Thus, the present invention is also directed to such nucleic acid and protein fragments.

EXAMPLES

The present invention is further detailed in the following Examples, which are offered by way of illustration and are not intended to limit the invention in any manner. Standard techniques well known in the art or the techniques specifically described below are utilized.

Example 1

Yeast Two-Hybrid System

The principles and methods of the yeast two-hybrid systems have been described in detail (Bartel and Fields, 1997). The following is thus a description of the particular procedure that was used, which was applied to all proteins.

The cDNA encoding the bait protein was generated by PCR from brain cDNA. Gene-specific primers were synthesized with appropriate tails added at their 5' ends to allow recombination into the vector pGBTQ. The tail for the forward primer was 5'-GCAGGAAACAGCTATGACCAT ACAGTCAGCGGCCGCCACC-3' (SEQ ID NO: 1) and the tail for the reverse primer was 5'-ACGGCCAGT CGCGTGGAGTGTTATGTCATGCGGCCGCTA-3' (SEQ ID NO:2). The tailed PCR product was then introduced by recombination into the yeast expression vector pGBTQ, which is a close derivative of pGBTC (Bartel et al., 1996) in which the polylinker site has been modified to include M13 sequencing sites. The new construct was selected directly in the yeast J693 for its ability to drive tryptophane synthesis (genotype of this strain: Mat α, ade2, his3, leu2, trp1, URA3::GAL1-lacZ LYS2::GAL1-HIS3 gal4del gal80del cyhR2). In these yeast cells, the bait is produced as a C-terminal fusion protein with the DNA binding domain of the transcription factor Gal4 (amino acids 1 to 147). A total human brain (37 year-old male Caucasian) cDNA library cloned into the yeast expression vector pACT2 was purchased from Clontech (human brain MATCHMAKER cDNA, cat. # HL4004AH), transformed into the yeast strain J692 (genotype of this strain: Mat α, ade2, his3, leu2, trp1, URA3::GAL1-lacZ LYS2::GAL1-HIS3 gal4del gal80del cyhR2), and selected for the ability to drive leucine synthesis. In these yeast cells, each cDNA is expressed as a fusion protein with the transcription activation domain of the transcription factor Gal4 (amino acids 768 to 881) and a 9 amino acid hemagglutinin epitope tag. J693 cells (Mat α type) expressing the bait were then mated with J692 cells (Mat α type) expressing proteins from the brain library. The resulting diploid yeast cells expressing proteins interacting with the bait protein were selected for the ability to synthesize tryptophane, leucine, histidine, and β-galactosidase. DNA was prepared from each clone, transformed by electroporation into *E. coli* strain KC8 (Clontech KC8 electrocompetent cells, cat # C2023-1), and the cells were selected on ampicillin-containing plates in the absence of either tryptophane (selection for the bait plasmid) or leucine (selection for the brain library plasmid). DNA for both plasmids was prepared and sequenced by di-deoxynucleotide chain termination method. The identity of the bait cDNA insert was confirmed and the cDNA insert from the brain library plasmid was identified using BLAST program against public nucleotides and protein databases. Plasmids from the brain library (preys) were then individually transformed into yeast cells together with a plasmid driving the synthesis of lamin fused to the Gal4 DNA binding domain. Clones that gave a positive signal after β-galactosidase assay were considered false-positives and discarded. Plasmids for the remaining clones were transformed into yeast cells together with plasmid for the original bait. Clones that gave a positive signal after β-galactosidase assay were considered true positives.

Examples 2–33

Identification of Protein—Protein Interactions

A yeast two-hybrid system as described in Example 1 using amino acids of the bait as set forth in Table 36 was performed. The clone that was identified by this procedure for each bait is set forth in Table 36 as the prey. The "aa" refers to the amino acids of the bait or prey. The GenBank and Sw-Pr columns refer to the GenBank and Swiss Protein accession numbers, respectively.

One novel protein, identified as PN7740, was discovered in these Examples. The cDNA sequence and protein sequence for PN7740 are set forth in Tables 34 and 35, respectively.

TABLE 34 cDNA Sequence of PN7740 (SEQ ID NO:3)

| |
|---|
| CGAGAATTTCCAGCAGGCAAGGCAGTGGCCGCTTTGACTGCTTGCTTCGGAGATCCGAGACGAC |
| GGAGAAGGCACTCTTATTTACCGACCAAGAAAGCTCCTCCCCCGTCCTCCGTTAGCTAATTAAA |
| ACATTTTTCAGGGACGTAGCCATCCAGAGACATTCCATTATTGTTCCATTGACCTTTCCCTCAT |
| CACTGAGTCCTTTGGAGCTGAGTTATGTCAACAGCTGCCTTAATTACTTTGGTCAGAAGTGGTG |
| GGAACCAGGTGAGAAGGAGAGTGCTGCTAAGCTCCCGCCTGCTGCAGGACGACAGGCGGGTGAC |
| ACCCACGTGCCACAGCTCCACTTCAGAGCCTAGGTGTTCTCGGTTTGACCCAGATGGTAGTGGG |
| AGTCCAGCTACCTGGGACAATTTTGGGATCTGGGATAACCGCATTGATGAGCCAATTCTGCTGC |

TABLE 34-continued cDNA Sequence of PN7740 (SEQ ID NO:3)

CACCCAGCATTAAGTATGGCAAGCCAATTCCCAAAATCAGCTTCCAAAATGTGGGTGCGCCTC
ACAGATTGGCAAACGGAAAGAGAATGAAGATCGGTTTGACTTCGCTCAGCTCACAGATGAGGTC
CTGTACTTTGCAGTGTATGATGGACACGGTGGACCTGCAGCAGCTGATTTCTGTCATACCCACA
TGGAGAAATGTATTATGGATTTGCTTCCTAAGGAGAAGAACTTGGAAACTCTGTTGACCTTGGC
TTTTCTAGAAATAGATAAAGCCTTTTCGAGTCATGCCCGCCTGTCTGCTGATGCAACTCTTCTG
ACCTCTGGGACTACTGCAACAGTAGCCCTATTGCGAGATGGTATTGAACTGGTTGTAGCCAGTG
TTGGGACAGCCGGGCTATTTTGTGTAGAAAAGGAAAACCCATGAAGCTGACCATTGACCATAC
TCCAGAAAGAAAAGATGAAAAAGAAAGGATCAAGAAATGTGGTGGTTTTGTAGCTTGGAATAGT
TTGGGGCAGCCTCACGTAAATGGCAGGCTTGCAATGACAAGAAGTATTGGAGATTTGGACCTTA
AGACCAGTGGTGTCATAGCAGAACCTGAAACTAAGAGGATTAAGTTACATCATGCTGATGACAG
CTTCCTGGTCCTCACCACAGATCCAATTAACTTCATGGTGAATAGTCAAGAGATTTGTGACTTT
GTCAATCAGTGCCATGATCCCAACGAAGCACCCCATGCGGTGACTGAACAGGCAATACAGTACG
GTACTGAGGATAACAGTACTGCAGTAGTACTGCCTTTTGGTGCCTGGGGAAAATATAAGAACTC
TGAAATCAACTTCTCATTCAGCAGAAGCTTTGCCTCCAGTGGACGATGGGCCTGATTACCAGCT
GGGACTTAGAGTTTCTGTGCAAOAGTTTTTCACTGAGCATGTCAAGAAACTGATAAGATCAAAA
AGGTCTCCTAACTCACTAGATCACCGCACAAGTCAGTGTAAACCACTTAGATAGTAGTTTTTTC
ATAAATGCTCATCATATTTATGTTCCGOTGTACATGTTCAGTATAAATATATGTGTACTGAAGC
TACTGTGAGTCTTTAAATGGAAAGAGCAAATGAGAAGTGGTTTGGATACACTTGATGAGAGATG
AGAGTGTCACATTAATAATTTTTAAGACTCTTAGGCAGCTATGGGTTTCTTTTGATCATTTTTG
TTCTTTATTCATTTGAACACGTTTTTGAAGTTCTTCAAAACTAGTCAGTTTGAATTTTGACAGC
TATTCAATATGTGATCTCCAAGTTTAAAAAAATTTTTTTCCAGACTTCCCTAATCCTAAAATGC
GAGTTTTTATTTTTAATAACTGTACCAAGGAATAAGTATGAAAACAGTTCTCTGTTACCATATT
TTGTATTCTGGACCACTTACTGGTGAAAGCAACCATGCAAAAGAAATTAATTTGGCCAGGCACA
GTGGCTCATGCCTGTAATCCCAAATTGCTGGGATTACAGCACTGTGCCCTCCTAGGAAATTATT
TTTTAAGTGAAATTTTATTTTTATTTTTTTAGGATTTTGGTAGAGAATGAGTAGGCCTACTCA
TCAATATCAAACAGGACATTTAGTTTCTTTCCTTAGAACAGACATAAATTTAATTTCATGGTAA
TATGATAATAAGAAAATGCTTCTATTTTTCTTTAGCACCTCCATGGTTCTCATATACCCATGTC
TGTAAAAAGTGACATGAGAATTTTGTTGGGTTACATTTTATTGTATTTATTAGATTCGCTTATA
TAGATGACTTACGCAGAAATAAAGTCATGTCTTTAGAAGGTGAACAAGCCAACTTGTGATGGCC
TGCCTTTTGCTTTTGGCAGTTGGGATGAGAACAATTGACTCTCCCATTGGTTGTTACATAGTTG
AAATGGTGCGTTGGTGGTCATACTTAGTGTTCTAGGCTGTGAAATCATGGAGTTCTTCCACTTC
CAAGAATGACTCATTTGCTGTTGGATTCTAGTACAGAATTTAGCAGCCTGATGTGTCCCCAAAC
TGATTTAATTTCTACTGAAGTGCCCTTGTGTACATTTGTTTTGTAATTTACCAAAGTACTACCT
GAGTGTATAATGACTCCTGCAGTGAGTTAATGTAATTGCTGCTTTGACCATTGTTTTAAATCTG
TCTACTAGAGTAACTCTGACCAGAATGAAATCACATTATCTCAGTGTTCAAAATATCATTCTAA
TAAAGTACATGCATTAAACAATTTTAAAAAAAACAAAAAAAAAAAA

TABLE 35

Protein Sequence of PN7740 (SEQ ID NO:4)

MSTAALITLVRSGGNQVRRRVLLSSRLLQDDRRVTPTCHSSTSEPRCSRFDPDGSGSPATWDNFGIW

DNRTDEPTLLPPSTKYGKPIPKTSLENVGCASQTGKRKENEDRFDFAQLTDEVLYFAVYDGHGGPAA

ADFCHTHMEKCIMDLLPKEKNLETLLTLAFLETDKAFSSHARLSADATLLTSGTTATVALLRDGTEL

VVASVGDSRATLCRKGKPMKLTTDHTPERKDEKERTKKCGGFVAWNSLGQPHVNGRLAMTRSIGDLD

LKTSGVIAEPBTKRTKLHHADDSFLVLTTDGINFMVNSQETCDFVNQCHDPNEAAHAVTEQATQYGT

EDNSTAVVVPFGAWGKYKNSEINFSFSRSFASSGRWA

TABLE 36

| Ex. | Bait | aa | GenBank | Sw-Pr | Prey | aa | GenBank | Sw-Pr |
|---|---|---|---|---|---|---|---|---|
| 2 | BAT3 | 271–480 | M33519 | P46379 | glypican | 400–483 | X54232 | P35052 |
| 3 | BAT3 | 740–1040 | M33519 | P46379 | LRP2 | 1–304 | U33837 | P98164 |
| 4 | BAT3 | 740–1040 | M33519 | P46379 | LRPAP1 | 11–361 | M63959 | P30533 |
| 5 | BAT3 | 740–1040 | M33519 | P46379 | transthyretin | 7–148 | X59498 | P02766 |
| 6 | Fe65 | 360–552 | L77864 | | PN7740 | 27–322 | | |
| 7 | Mint 1 | 739–837 | AF047347 | Q02410 | GS | 49–212 | X59834 | P15104 |
| 8 | Mint 1 | 447–758 | AF047347 | Q02410 | KIAA0427 | 364–589 | AB007887 | |
| 9 | PS1 | 1–91 | L42110 | Q15720 | Mint 1 | 471–822 | AF047347 | Q02410 |
| 10 | CASK | 306–574 | AF032119 | Q43215 | dystrophin | 909–1280 | M18533 | P11532 |
| 11 | CIB | 1–191 | U82226 | Q99828 | S1P | 442–619 | NM_003791 | |
| 12 | Mint2 | 1–210 | AF047348 | Q99767 | S1P | 765–859 | NM_003791 | |
| 13 | PS1 | 1–91 | L42110 | Q15720 | P-glycerate DH | 1–266 | NM_006623 | O43175 |
| 14 | PS1 | 1–91 | L42110 | Q15720 | beta-ETF | 31–242 | X71129 | P38117 |
| 15 | PS1 | 1–91 | L42110 | Q15720 | GAPDH | 2–190 | M17851 | P04406 |
| 16 | PS2 | 1–97 | L44577 | P49810 | GAPDH | 2–190 | M17851 | P04406 |
| 17 | CIB | 1–137 | U82226 | Q99828 | ATP synthase | 229–459 | X03559 | P06576 |
| 18 | KIAA0443 | 901–1200 | AB007903 | | PI-4-kinase | 567–854 | L36151 | P42356 |
| 19 | KIAA0443 | 901–1200 | AB007903 | | 5HT-2A R | 27–132 | X57830 | P28223 |
| 20 | KIAA0351 | 301–557 | AB002349 | | TRIO | 475–733 | U42390 | |
| 21 | CIB | 1–191 | U82226 | Q99828 | MLK2 | 305–549 | X90846 | Q02779 |
| 22 | BAX | 50–107 | L22474 | Q07812 | slo K+ channel | 643–993 | U13913 | |
| 23 | FAK2 | 673–866 | L49207 | Q14289 | SUR1 | 121–270 | AF087138 | Q09428 |
| 24 | Mint2 | 1–210 | AF047348 | Q99767 | PDE-9A | 269–593 | AF048837 | O76083 |
| 25 | CIB | 1–191 | U82226 | Q99828 | SCD2 | 320–359 | Y13647 | O00767 |
| 26 | rab11 | 1–137 | X56740 | P24410 | FAK | 726–1003 | L13616 | Q14291 |
| 27 | FAK | 724–1052 | L13616 | Q14291 | casein kinase II | 264–351 | M55268 | P19784 |
| 28 | FAK | 724–1052 | L13616 | Q14291 | GST trans. M3 | 15–226 | J05459 | P21266 |
| 29 | bcr | 1206–1271 | NM_004327 | P11274 | PSD95 | 110–266 | NM_001365 | P78352 |
| 30 | bcr | 1206–1271 | NM_004327 | P11274 | DLG3 | 94–506 | U49089 | Q92796 |
| 31 | bcr | 856–1226 | NM_004327 | P11274 | Semaphorin F | 670–821 | | |
| 32 | bcr | 1206–1271 | NM_004327 | P11274 | HTF4A | 296–494 | M83233 | Q99081 |
| 33 | bcr | 1134–1271 | NM_004327 | P11274 | SRCAP | 1916–2088 | AF143946 | |

Example 34

Yeast Two-Hybrid System

The principles and methods of the yeast two-hybrid systems have been described in detail (Bartel and Fields, 1997). The following is thus a description of the particular procedure that was used for the finding of the interaction between PSD95 and PN7740.

The cDNA encoding the bait protein was generated by PCR from cDNA prepared from a desired tissue. Gene-specific primers were synthesized with appropriate short tails added at their 5' ends to provide homology to the vector pGBT.Q. The tail for the forward primer was 5'-CCGCCACCATGGAATTA-3' (SEQ ID NO:5) and the tail for the reverse primer was 5'-TGCGGCCGCTAGTCGA-3' (SEQ ID NO:6). The tailed PCR product was then subjected to a secondary PCR reaction that extended the length of the tails and therefore the homology to the vector to facilitate cloning by homologous recombination. The secondary PCR reaction involves several steps, starting with the extension of the 3' ends of each tail by direct priming on the vector. This extension creates homology to secondary primers that correspond to vector sequences further upstream and downstream, respectively, from the original short tails. The secondary forward primer was 5'-CGCAGGAAACAGCTATGA-3' (SEQ ID NO:7) and the secondary reverse primer was 5'-TTGTAAAACGACGGCCAG-3' (SEQ ID NO:8). The secondary primers allow complementary strand synthesis of the extended tailed product. Once both 3' ends of the bait fragment have been extended it is amplified with the secondary primers. The product is then introduced by recombination into the yeast expression vector pGBT.Q, which is a close derivative of pGBT.C (Bartel et al. 1996) in which the polylinker site has been modified to include M13 sequencing sites. The new construct was selected directly in the yeast strain PNY200 for its ability to drive tryptophane synthesis (genotype of this strain: MAT α trp1-901 leu2-3,112 ura3-52 his3-200 ade2 gal4Δgal80). In these yeast cells, the bait was produced as a C-terminal fusion protein with the DNA binding domain of the transcription factor Gal4 (amino acids 1 to 147). Prey libraries were transformed into the yeast strain BK100 (genotype of this strain: MATαtrp1-901 leu2-3,112 ura3-52 his3-200 gal4Δgal80LYS2::GAL-HIS3 GAL2-ADE2 met2::GAL7-lacZ), and selected for the ability to drive leucine synthesis. In these yeast cells, each cDNA was expressed as a fusion protein with the transcription activation domain of the transcription factor Gal4 (amino acids 768 to 881) and a 9 amino acid hemagglutinin epitope tag. PNY200 cells (MATα mating type), expressing the bait, were then mated with BK100 cells (MATa mating type), expressing prey proteins from a prey library. The resulting diploid yeast cells expressing proteins interacting with the bait protein were selected for the ability to synthesize tryptophan, leucine, histidine, and adenine. DNA was prepared from each clone, transformed by electroporation into E. coli strain KC8 (Clontech KC8 electrocompetent cells, Catalog No. C2023-1), and the cells were selected on ampicillin-containing plates in the absence of either tryptophane (selection for the bait plasmid) or leucine (selection for the library plasmid). DNA for both plasmids was prepared and sequenced by the dideoxynucleotide chain termination method. The identity of the bait cDNA insert was confirmed and the cDNA insert from the prey library plasmid was identified using the BLAST program to search against public nucleotide and protein databases. Plasmids from the prey library were then individually transformed into yeast cells together with a plasmid driving the synthesis of lamin and 5 other test proteins, respectively, fused to the Gal4 DNA binding domain. Clones that gave a positive signal in the p-galactosidase assay were considered false-positives and discarded. Plasmids for the remaining clones were transformed into yeast cells together with the original bait plasmid. Clones that gave a positive signal in the β-galactosidase assay were considered true positives.

In this example, amino acids 149–255 of PSD95 (GenBank (GB) accession No. NM_001365) was used as bait. One clone that was identified by this procedure included amino aicds 27–321 of novel protein PN7740.

Example 35

Generation of Polyclonal Antibody Against BAT3-Glypican Complex

As shown above, BAT3 interacts with glypican to form a complex. A complex of the two proteins is prepared, e.g., by mixing purified preparations of each of the two proteins. If desired, the protein complex can be stabilized by cross-linking the proteins in the complex by methods known to those of skill in the art. The protein complex is used to immunize rabbits and mice using a procedure similar to the one described by Harlow et al. (1988). This procedure has been shown to generate Abs against various other proteins (for example, see Kraemer et al., 1993).

Briefly, purified protein complex is used as an immunogen in rabbits. Rabbits are immunized with 100 μg of the protein in complete Freund's adjuvant and boosted twice in three-week intervals, first with 100 μg of immunogen in incomplete Freund's adjuvant, and followed by 100 μg of immunogen in PBS. Antibody-containing serum is collected two weeks thereafter. The antisera is preadsorbed with BAT3 and glypican, such that the remaining antisera comprises antibodies which bind conformational epitopes, i.e., complex-specific epitopes, present on the BAT3-glypican complex but not on the monomers.

Polyclonal antibodies against each of the complexes set forth in Tables 1–33 are prepared in a similar manner by mixing the specified proteins together, immunizing an animal and isolating antibodies specific for the protein complex, but not for the individual proteins.

Polyclonal antibodies against the novel protein set forth in Table 35 is prepared in a similar manner by immunizing an animal with the protein and isolating antibodies specific for the protein.

Example 36

Generation of Monoclonal Antibodies Specific for BAT3-Glypican Complex

Monoclonal antibodies are generated according to the following protocol. Mice are immunized with immunogen comprising BAT3-glypican complexes conjugated to keyhole limpet hemocyanin using glutaraldehyde or EDC as is well known in the art. The complexes can be prepared as described in Example 35 may also be stabilized by crosslinking. The immunogen is mixed with an adjuvant. Each mouse receives four injections of 10 to 100 μg of immunogen, and after the fourth injection, blood samples are taken from the mice to determine if the serum contains antibodies to the immunogen. Serum titer is determined by ELISA or RIA. Mice with sera indicating the presence of antibody to the immunogen are selected for hybridoma production.

Spleens are removed from immune mice and a single-cell suspension is prepared (Harlow et al., 1988). Cell fusions are performed essentially as described by Kohler and Milstein (1975). Briefly, P3.65.3 myeloma cells (American Type Culture Collection, Rockville, Md.) or NS-1 myeloma cells are fused with immune spleen cells using polyethylene glycol as described by Harlow et al. (1988). Cells are plated at a density of 2×10$^5$ cells/well in 96-well tissue culture plates. Individual wells are examined for growth, and the supernatants of wells with growth are tested for the presence of BAT3-glypican complex-specific antibodies by ELISA or RIA using BAT3-glypican complex as target protein. Cells in positive wells are expanded and subcloned to establish and confirm monoclonality.

Clones with the desired specificities are expanded and grown as ascites in mice or in a hollow fiber system to produce sufficient quantities of antibodies for characterization and assay development. Antibodies are tested for binding to BAT3 alone or to glypican alone, to determine which are specific for the BAT3-glypican complex as opposed to those that bind to the individual proteins.

Monoclonal antibodies against each of the complexes set forth in Tables 1–33 are prepared in a similar manner by mixing the specified proteins together, immunizing an animal, fusing spleen cells with myeloma cells and isolating clones which produce antibodies specific for the protein complex, but not for the individual proteins.

Monoclonal antibodies against the novel protein set forth in Table 35 are prepared in a similar manner by immunizing an animal with the protein, fusing spleen cells with myeloma cells and isolating clones which produce antibodies specific for the protein.

Example 37

In vitro Identification of Modulators for BAT3-Glypican Interaction

The invention is useful in screening for agents, which modulate the interaction of BAT3 and glypican. The knowledge that BAT3 and glypican form a complex is useful in designing such assays. Candidate agents are screened by mixing BAT3 and glypican (a) in the presence of a candidate agent and (b) in the absence of the candidate agent. The amount of complex formed is measured for each sample. An agent modulates the interaction of BAT3 and glypican if the amount of complex formed in the presence of the agent is greater than (promoting the interaction), or less than (inhibiting the interaction) the amount of complex formed in the absence of the agent. The amount of complex is measured by a binding assay that shows the formation of the complex, or by using antibodies immunoreactive to the complex.

Briefly, a binding assay is performed in which immobilized BAT3 is used to bind labeled glypican. The labeled glypican is contacted with the immobilized BAT3 under aqueous conditions that permit specific binding of the two proteins to form an BAT3-glypican complex in the absence of an added test agent. Particular aqueous conditions may be selected according to conventional methods. Any reaction condition can be used, as long as specific binding of BAT3-glypican occurs in the control reaction. A parallel binding assay is performed in which the test agent is added to the reaction mixture. The amount of labeled glypican bound to the immobilized BAT3 is determined for the reactions in the absence or presence of the test agent. If the amount of bound, labeled glypican in the presence of the test agent is different than the amount of bound labeled glypican in the absence of the test agent, the test agent is a modulator of the interaction of BAT3 and glypican.

Candidate agents for modulating the interaction of each of the protein complexes set forth in Tables 1–33 are screened in vitro in a similar manner.

Example 38

In Vivo Identification of Modulators for BAT3-Glypican Interaction

In addition to the in vitro method described in Example 37, an in vivo assay can also be used to screen for agents that modulate the interaction of BAT3 and glypican. Briefly, a yeast two-hybrid system is used in which the yeast cells express (1) a first fusion protein comprising BAT3 or a fragment thereof and a first transcriptional regulatory protein sequence, e.g., GAL4 activation domain, (2) a second fusion protein comprising glypican or a fragment thereof and a second transcriptional regulatory protein sequence, e.g., GAL4 DNA-binding domain, and (3) a reporter gene, e.g., β-galactosidase, which is transcribed when an intermolecular complex comprising the first fusion protein and the second fusion protein is formed. Parallel reactions are performed in the absence of a test agent as the control and in the presence of the test agent. A functional BAT3-glypican complex is detected by detecting the amount of reporter gene expressed. If the amount of reporter gene expression in the presence of the test agent is different than the amount of reporter gene expression in the absence of the test agent, the test agent is a modulator of the interaction of BAT3 and glypican.

Candidate agents for modulating the interaction of each of the protein complexes set forth in Tables 1–33 are screened in vivo in a similar manner.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

BIBLIOGRAPHY

Abe, K. and Kimura, H. (1996). *J Neurochem* 67:2074–2078.
Aksenov, M. Y. et al. (1996). *J Neurochem* 66:2050–2056.
Aksenov, M. Y. et al. (1997). *Free Radic Res* 27:267–281.
Albert, M. S. (1996). *Proc Natl Acad Sci USA* 93:13547–13551.
Alvarez, A. et al. (1998). *J Neurosci* 18:3213–3223.
Anderson, J. P. et al. (1991). *Neurosci Lett* 128:126–128.
Annaert, W. G. et al. (1999). *J Cell Biol* 147:277–294.
Araki, W. et al. (1991). *Biochem Biophys Res Commun* 181:265–271.
Aronheim et al., (1997). *Mol. Cell. Biol* 17:3094–3102.
Ashall, F. and Goate, A. M. (1994). *Trends Biochem Sci* 19:42–46.
Ashcroft, F. M. (1996). *Horm Metab Res* 28:456–463.
Ashcroft, S. J. H. and Ashcroft, F. M. (1992). *Biochim Biophys Acta* 1175:45–49.
Askanas, V. et al. (1992). *Neurosci Lett* 143:96–100.
Ausubel, F. M. et al. (1992). *Current Protocols in Molecular Biology*, (J. Wiley and Sons, NY).
Avraham, S. et al. (1995). *J Biol Chem* 270:27742–27751.
Bachurin, S. et al. (1999). *Ann N Y Acad Sci* 890:155–166.
Barger, S. W. et al. (1995). *J Neurochem* 64:2087–2096.
Barger, S. W. and Mattson, M. P. (1995). *Biochem J* 311:45–47.
Barger, S. W. and Mattson, M. P. (1996). *Brain Res Mol Brain Res* 40:116–126.
Bartel, P. L. et al. (1993). "Using the 2-hybrid system to detect protein—protein interactions." In: *Cellular Interactions in Development: A Practical Approach*, Oxford University Press, pp. 153–179.
Bartel, P. L. et al. (1996). *Nat Genet* 12:72–77.
Bartel, P. L. and Fields, S. (1997). *The Yeast Two-Hybrid System*. New York: Oxford University Press.
Baum, L. et al. (1992). *Brain Res* 573:126–132.
Beal, M. F. (1996). *Curr Opin Neurobiol* 6:661–666.
Beal, M. F. (1998). *Biochim Biophys Acta* 1366:211–223.
Begley, J. G. et al. (1999). *J Neurochem* 72:1030–1039.
Behl, C. et al. (1992). *Biochem Biophys Res Commun* 186:944–950.
Berg, M. M. et al. (1997). *J Neurosci Res* 50:979–989.
Beyreuther, K. et al. (1996). *Ann NY Acad Sci* 777:74–76.
Blanco, G. et al. (1998). *Mamm Genome* 9:473–475.
Bodovitz, S. and Klein, W. L. (1996). *J Biol Chem* 271:4436–4440.
Borchelt, D. R. et al. (1996). *Neuron* 17:1005–1013.
Borg, J. P. et al. (1998a). *J Biol Chem* 273:31633–31636.
Borg, J. P. et al. (1998b). *J Biol Chem* 273:14761–14766.
Borg, J. P. et al. (1999). *J Neurosci* 19:1307–1316.
Bowes, M. P. et al. (1994). *Exp Neurol* 129:112–119.
Braselmann, S. and McCormick, F. (1995). *EMBO J* 14:4839–4848.
Brion, J. P. (1998). *Acta Neurol Belg* 98:165–174.
Brown, M. S. and Goldstein, J. L. (1999). *Proc Natl Acad Sci USA* 96:11041–11048.
Bryan, J. et al. (1999). *Biochim Biophys Acta* 1461:285–303.
Butterfield, D. A. (1997). *Chem Res Toxicol* 10:495–506.
Buxbaum, J. D. et al. (1990). *Proc Natl Acad Sci USA* 87:6003–6006.
Buxbaum, J. D. et al. (1993). *Proc Natl Acad Sci USA* 90:9195–9198.
Caporaso, G. L. et al. (1992). *Proc Natl Acad Sci USA* 89:3055–3059.

Caputi, A. et al. (1997). *J Neurochem* 68:2523–2529.
Chalimoniuk, M. and Strosznajder, J. B. (1998). *Mol Chem Neuropathol* 35:77–95.
Chen, W. et al. (1998). *Mol Biol Cell* 9:3241–3257.
Chen, R. W. et al. (1999). *J Neurosci* 19:9654–9662.
Chevray, P. M. and Nathans, D. N. (1992). *Proc. Natl. Acad. Sci. USA* 89:5789–5793.
Christie, M. J. (1995). *Clin Exp Pharmacol Physiol* 22:944–951.
Citron, M. et al. (1998). *Neurobiol Dis* 5:107–116.
Cruts, M. and Van Broeckhoven, C. (1998). *Hum Mutat* 11:183–190.
Cummings, J. L. et al. (1998). *Neurology* 51:S2–17.
De Bleecker, J. L. et al. (1996). *J Neuropathol Exp Neurol* 55:563–577.
Debant, A. et al. (1996). *Proc Natl Acad Sci USA* 93:5466–5471.
De Strooper, B. et al (1999). *Nature* 398:518–522.
Dickson, D. W. (1997). *J Neuropathol Exp Neurol* 56:321–339.
Diekmann, D. et al. (1995). *EMBO J* 14:5297–5305.
Dierick, H. and Bejsovec, A. (1999). *Curr Top Dev Biol* 43:153–190.
Dimitratos S D et al. (1999). Bioessays 21:912–921.
Di Rocco, G. et al. (1997). *Mol Cell Biol* 17:1244–1253.
Doan, A. et al. (1996). *Neuron* 17:1023–1030.
Dorow, D. S. et al. (1993). *Eur J Biochem* 213:701–710.
Doyle, E. et al. (1990). *Neurosci Lett* 115:97–102.
Duff, K. et al (1996). *Nature* 383:710–713.
Duncan, E. A. et al. (1997). *J Biol Chem* 272:12778–12785.
Ermekova, K. S. et al. (1997). *J Biol Chem* 272:32869–32877.
Etcheberrigaray, R. et al. (1993). *Proc Natl Acad Sci USA* 90:8209–8213.
Fagarasan, M. O. and Aisen, P. S. (1996). *Brain Res* 723:231–234.
Farber, S. A. et al. (1995). *J Neurosci* 15:7442–7451.
Farlow, M. R. (1998). *Am J Health Syst Pharm* 55 Suppl 2:S5–10.
Fields, S. and Song, O-K. (1989). *Nature* 340:245–246.
Fisher, D. A. et al. (1998). *J Biol Chem* 273:15559–15564.
Forloni, G. et al. (1997). *J Neurochem* 68:319–327.
Furukawa, K. et al. (1996a). *Nature* 379:74–78.
Furukawa, K. et al. (1996b). *J Neurochem* 67:1882–1896.
Garbay, B. et al. (1997). *Dev Brain Res* 98:197–203.
Garbay, B. et al. (1998). *J Neurochem* 71:1719–1726.
Gillardon, F. et al. (1996). *Brain Res* 706:169–172.
Girault, J. A. et al. (1999). *Trends Neurosci* 22:257–263.
Goodman, Y. and Mattson, M. P. (1996). *Brain Res* 706:328–332.
Gschwind, M. et al. (1996). *Ann NY Acad Sci* 777:293–296.
Gunnersen, D. and Haley, B. (1992). *Proc Natl Acad Sci USA* 89:11949–11953.
Guo, Q. et al. (1996). *Neuroreport* 8:379–383.
Guo, Q. et al. (1998a). *Nat Med* 4:957–962.
Guo, Q. et al. (1998b). *J Biol Chem* 273:12341–12351.
Guo, Q. et al. (1999a). *J Neurosci Res* 56:457–470.
Guo, Q. et al. (1999b). *Nat Med* 5:101–106.
Haass, C. and De Strooper, B. (1999). *Science* 286:916–919.
Hardy, J. (1997). *Trends Neurosci* 20:154–159.
Hardy, J. and Gwinn-Hardy, K. (1998). *Science* 282:1075–1079.
Harlow et al. (1988). *Antibodies: A Laboratory Manual* (Cold Spring Harbor Laboratory, Cold Spring Harbor, N.Y.).
Heron, L. et al. (1998). *Proc Natl Acad Sci USA* 95:8387–8391.
Heron, L. et al. (1999). *Diabetes* 48:1873–1876.
Hoffman, E. P. (1999). *Arch Pathol Lab Med* 123:1050–1052.
Holm, N. R. et al. (1997). *Proc Natl Acad Sci USA* 94:1002–1006.
Hughes, S. R. et al. (1998). *Proc Natl Acad Sci USA* 95:3275–3280.
Huber, G. et al. (1993). *Brain Res* 603:348–352.
Huber, G. et al. (1997). *Neuroscience* 80:313–320.
Hussain, I. et al. (1999). *Mol Cell Neurosci in press*: get cite
Hutton, M. and Hardy, J. (1997). *Hum Mol Genet* 6:1639–1646.
Ii, K. (1995). *Drugs Aging* 7:97–109.
Iimoto, D. S. et al. (1990). *Brain Res* 507:273–280.
Inagaki, N. et al. (1995). *Science* 270:1166–1170.
Inagaki, N. et al. (1997). *FEBS Lett* 409:232–236.
Inestrosa, N. C. and Alarcon, R. (1998). *J Physiol Paris* 92:341–344.
Inagaki, N. and Seino, S. (1998). *Jpn J Physiol* 48:397–412.
Ishii, K. et al. (1997). *Neurosci Lett* 228:17–20.
Ishikawa, K. et al. (1997). *DNA Res* 4:307–313.
Iversen, L. L. et al. (1995). *Biochem J* 311:1–16.
Jaffrey, S. R. et al. (1998). *Neuron* 20:115–124.
Jan, L. Y. and Jan, Y. N. (1997). *Curr Opin Cell Biol* 9:155–160.
Jin, L-W. et al. (1994). *Proc Natl Acad Sci USA* 91:5461–5470.
Jin, L-W. and Saitoh, T. (1995). *Drugs Aging* 6:136–149.
Jin, Y. J. et al. (1992). *J Biol Chem* 267:10942–10945.
Johnston, H. et al. (1999). *J Biol Chem* 274:16370–16376.
Joseph, R. and Han, E. (1992). *Biochem Biophys Res Commun* 184:1441–1447.
Kalaria, R. N. et al. (1996a). *Neurodegeneration* 5:497–503.
Kalaria, R. N. et al. (1996b). *Neurobiol Aging* 17:687–693.
Katoh, M. et al. (1995). *Oncogene* 10:1447–1451.
Keller, J. N. and Mattson, M. P. (1998). *Rev Neurosci* 9:105–116.
Kim, J. H. et al. (1998). *Neuron* 20:683–691.
Kim, T. W. and Tanzi, R. E. (1997). *Curr Opin Neurobiol* 7:683–688.
Kim, T. W. et al. (1992). *Proc Natl Acad Sci USA* 89:11642–11644.
Kistner U et al. (1993). *J Biol Chem* 268:4580–4583.
Kohler, G. and Milstein, C. (1975). *Nature* 256, 495–497.
Komori, N. et al. (1997). *Mol Brain Res* 49:103–112.
Kong, J. and Anderson, J. E. (1999). *Brain Res* 839:298–304.
Korenberg, J. R. et al. (1994). *Genomics* 22:88–93.
Kornau, H. C. et al. (1995). *Science* 269:1737–1740.
Kosik, K. S. (1999). *Nat Med* 5:149–150.
Kounnas, M. Z. et al. (1995). *J Biol Chem* 270:13070–13075.
Kraemer, F. B. et al. (1993). *J Lipid Res.* 34, 663–672.
Krebs, E. G. et al. (1988). *Cold Spring Harb Symp Quant Biol* 53 Pt 1:77–84.
Kruman, I. et al. (1997). *J Neurosci* 17:5089–5100.
LaFerla, F. M. et al. (1997). *J Clin Invest* 100:310–320.
Lanier, L. M. and Gertler, F. B. (2000). *Curr Opin Neurobiol* 10:80–87.
Lau, L. F. et al. (1996). *J Biol Chem* 271:21622–21628.
Laube, G. et al. (1996). *Brain Res Mol Brain Res* 42:51–61.
Lauritzen, I. et al. (1997). *J Neurochem* 69:1570–1579.
Lawson, K.(1996a). *Pharmacol Ther* 70:39–63.
Lawson, K. (1996b). *Clin Sci* 91:651–663.
Leanna, C. A. and Hannink, M. (1996). *Nucl. Acids Res.* 24:3341–3347.
Leblanc, A. C. et al. (1996). *J Neurochem* 66:2300–2310.

Lehmann, S. et al. (1997). *J Biol Chem* 272:12047–12051.
Lemere, C. A. et al. (1996). *Nature Med* 2:1146–1150.
Levesque, G. et al. (1999). *J Neurochem* 72:999–1008.
Leveugle, B. et al. (1997). *Neurochem Int* 30:543–548.
Li, H. L. et al. (1997). *J Neurobiol* 32:469–480.
Li, Y. M. et al. (2000a). *Proc Natl Acad Sci USA* 97:6138–6143.
Li, Y. M. et al. (2000b). *Nature* 405:689–694.
Lin, Y. F. et al. (2000). *EMBO J* 19:942–955.
Liu, Y. F. et al. (2000). *J Biol Chem* 275:19035–19040.
Lippa, C. F. (1999). *Int J Mol Med* 4:529–536.
Lorenzo, A. and Yankner, B. A. (1996). *Ann NY Acad Sci* 777:89–95.
Lovell, M. A. et al. (1998). *Neurology* 51:1562–1566.
Ma, J. Y. et al. (1996). *Neurobiol Aging* 17:773–780.
Manelli, A. M. and Puttfarcken, P. S. (1995). *Brain Res Bull* 38:569–576.
Marin, O. et al. (1996). *Int J Biochem Cell Biol* 28:999–1005.
Marin, O. et al. (1999). *J Biol Chem* 274:29260–29265.
Mark, R. J. et al. (1996). *Mol Neurobiol* 12:211–224.
Mark, R. J. et al. (1997). *J Neurochem* 68:255–264.
Masliah, E. et al. (1996). *Am J Pathol* 148:201–210.
Masliah, E. et al. (1997). *Neurosci* 78:135–146.
Mattson, M. P. (1994). *Ann NY Acad Sci* 747:50–76.
Mattson, M. P. (1997a). *Physiol Rev* 77:1081–1132.
Mattson, M. P. (1997b). *Alz Dis Review* 2:1–14.
Mattson, M. P. (1997c). *Neurosci Biobehav Rev* 21:193–206.
Mattson, M. P. and Duan, W. (1999). *J Neurosci Res* 58:152–166.
Mattson, M. P. and Furukawa, K. (1996). *Restor Neurol Neurosci* 9:191–205.
Mattson, M. P. et al. (1993a). *Trends Neurosci* 16:409–414.
Mattson, M. P. et al. (1993b). *Neuron* 10:243–254.
Mattson, M. P. et al. (1995). *J Neurochem* 65:1740–1751.
Mattson, M. P. et al. (1998). *J Neurochem* 70:1–14.
Mattson, M. P. et al. (1999). *Ann N Y Acad Sci* 893:154–175.
Mattson, M. P. et al. (1999). *Soc Neurosci Abstr* 25:1600.
Mattson, M. P. et al. (2000). *J Neurosci* 20:1358–1364.
McLoughlin, D. M. and Miller, C. C. J. (1996). *FEBS Lett* 397:197–200.
Meng, K. et al. (2000). *Proc Natl Acad Sci USA* 97:2603–2608.
Merched, A. et al. (1998). *FEBS Lett* 425:225–228.
Meziane, H. at al. (1998). *Proc Natl Acad Sci USA* 95:12683–12688.
Milward, E. A. et al (1992). *Neuron* 9:129–137.
Montoliu, C. et al. (1999). *Neuropharmacology* 38:1883–1891.
Mook-Jung, I. and Saitoh, T. (1997). *Neurosci Lett* 235:1–4. Erratum: *Neurosci Lett* 239:131.
Mucke, L. et al. (1995). *J Exp Med* 181:1551–1556.
Muller, B. M. et al. (1996). *Neuron* 17:255–265.
Muller, D. et al. (1995). *Synapse* 19:37–45.
Murphy, M. P. et al. (1999). *J Biol Chem* 274:11914–11923.
Murphy, M. P. et al. (2000). *J Biol Chem* 275:26277–26284.
Murayama, M. et al. (1998). *FEBS Lett* 433:73–77.
Nagano T et al. (1998). *J Biochem* 124:869–875.
Nagy, Z. et al. (1999). *Acta Neuropathol* 97:346–354.
Naik, U. P. et al. (1997). *J Biol Chem* 272:4651–4654.
Nakagawa, T. et al. (1996). *J Biol Chem* 271:12088–12094.
Nakamura, T. et al (1998). *Genes Cells* 3:395–403.
Nehring, R. B. et al. (2000). *J Neurosci* 20:156–162.
Neve, R. L. et al. (1990). *Prog Brain Res* 86:257–267.
Neville, C. M. et al. (1998). *J Biol Chem* 273:14046–14052.
Ninomiya, H. et al (1993). *J Cell Biol* 121:879–886.
Ninomiya, H. et al. (1994). *J Neurochem* 63:495–500.
Nitsch, R. M. et al. (1996). *J Biol Chem* 271:4188–4194.
Nohturfft, A. et al. (1999). *Proc Natl Acad Sci USA* 96:11235–11240.
Nonaka, I. (1994). *Rinsho Shinkeigaku* 34:1279–1281.
Octave, J. N. (1995). *Rev Neurosci* 6:287–316.
Okamoto, M. and Sudhof, T. C. (1997). *J Biol Chem* 272:31459–31464.
Okamoto, M. and Sudhof, T. C. (1998). *Eur J Cell Biol* 77:161–165.
Orlando, R. A. et al. (1997). *Proc Natl Acad Sci USA* 94:2368–2373.
Oyama, F. et al. (1998). *J Neurochem* 71:313–322.
Park, S. Y. et al. (2000). *J Biol Chem* 275:19768–19777.
Parsons, J. T. et al. (1994). *J Cell Sci* 18:109–113.
Pietrzik, C. U. et al. (1998). *Proc Natl Acad Sci USA* 95:1770–1775.
Price, D. L., et al. (1995). *Curr Opin Neurol* 8:268–274.
Rafael, J. A. et al. (1998). *Neuroreport* 9:2121–2125.
Rapoport, S. I. et al. (1996). *Neurodegeneration* 5:473–476.
Rawson, R. B. et al. (1997). *Mol Cell* 1:47–57.
Ray, W. J. et al., Ashall F, Goate AM (1998). *Mol Med Today* 4:151–157.
Renbaum, P. and Levy-Lahad, E. (1998). *Cell Mol Life Sci* 54:910–919.
Richardson, J. S. et al. (1996). *Ann NY Acad Sci* 777:362–367.
Roch, J-M. and Puttfarcken, P. S. (1996). *Alz ID Res Al* 1:9–16.
Roch, J-M. et al. (1992). *J Biol Chem* 267:2214–2221.
Roch, J-M. et al. (1993). *Ann N Y Acad Sci* 695:149–157.
Roch, J-M. et al. (1994). *Proc Natl Acad Sci USA* 91:7450–7454.
Rogers, J. et al. (1992a). *Proc Natl Acad Sci USA* 90:10016–10020.
Rogers, J. et al. (1992b). *Res Immunol* 143:624–630.
Rozemuller, J. M. et al. (1992). *Res Immunol* 143:646–649.
Russo, T. et al. (1998). *FEBS Lett* 434:1–7.
Sabo, S. L. et al. (1999). *J Biol Chem* 274:7952–7957.
Saitoh, T. et al. (1989). *Cell* 58:615–622.
Saitoh, T. et al. (1991). *Lab Invest* 64:596–616.
Saitoh, T. et al. (1994). The Biological Function of Amyloid β/A4 Protein Precursor. In: *Amyloid Protein Precursor in Development, Aging, and Alzheimer's Disease* (Masters, C. L. et al., eds), pp 90–99. Berlin: Springer-Verlag.
Saitoh, T. et al. (1995). Induction of Signal-transducing Pathways by APP Binding to a Cell Surface Receptor. In: *Research Advances in Alzheimer's Disease and Related Disorders* (Iqbal, J. A. et al. eds), pp 693–699. New York: John Wiley & Sons Ltd.
Saitoh, T. and Roch, J-M. (1995). *DN&P* 8:206–215.
Sakai, J. et al. (1998). *Mol Cell* 2:505–514.
Sans, N. et al. (2000). *J Neurosci* 20:1260–1271.
Sasaki, H. et al. (1995). *J Biol Chem* 270:21206–21219.
Sastre, M. et al. (1998). *J Biol Chem* 273:22351–22357.
Satin, L. S. (1996). *Endocrine* 4:191–198.
Schaller, M. D. (1997). *Soc Gen Physiol Ser* 52:241–255.
Schaller, M. D. and Parsons, J. T. (1994). *Curr Opin Cell Biol* 6:705–710.
Schlaepfer, D. D. et al. (1999). *Prog Biophys Mol Biol* 71:435–478.
Schubert, D. (1997).*Eur J Neurosci* 9:770–777.
Schulz, J. G. et al. (1998). *Eur J Neurosci* 10:2085–2093.
Schulze, H. et al. (1993). *J Neurochem* 60:1915–1922.
Schwarzman, A. L. et al. (1994). *Proc Natl Acad Sci USA* 91:8368–8372.
Seidah, N. G. et al. (1999a). *Ann N Y Acad Sci* 885:57–74.

Seidah, N. G. et al. (1999b). *Proc Natl Acad Sci USA* 96:1321–1326.
Selkoe, D. J. (1994a). *Annu Rev Neurosci* 17:489–517.
Selkoe, D. J. (1994b). *Annu Rev Cell Biol* 10:373–403.
Selkoe, D. J. (1994c). *J Neuropathol Exp Neurol* 53:438–447.
Selkoe, D. J. (1996a). *J Biol Chem* 271:18295–18298.
Selkoe, D. J. (1996b). *Cold Spring Harb Symp Quant Biol* 61:587–596.
Selkoe, D. J. (1997). *Science* 275:630–631.
Selkoe, D. J. (1998). *Trends Cell Biol* 8:447–453.
Selkoe, D. J. (1999). *Nature* 399:A23–A31.
Selkoe, D. J. and Wolfe, M. S. (2000). *Proc Natl Acad Sci USA* 97:5690–5692.
Shapiro, I. P. et al. (1991). *J Neurochem* 56:1154–1162.
Sheff, D. R. et al. (1999). *J Cell Biol* 145:123–139.
Shirahama, T. et al. (1982). *Am J Pathol* 107:41–50.
Siciliano, J. C. et al. (1996). *J Biol Chem* 271:28942–28946.
Simonian, N. A. and Coyle, J. T. (1996). *Annu Rev Pharmacol Toxicol* 36:83–106.
Sinha, S. and Lieberburg, I. (1999). *Proc Natl Acad Sci USA* 96:11049–11053.
Sisodia, S. S. (1992). *Proc Natl Acad Sci USA* 89:6075–6079.
Small, D. H. et al. (1994). *J Neurosci* 14:2117–2127.
Smith-Swintosky, V. L. et al. (1994). *J Neurochem* 63:781–784.
Snyder, S. E. et al. (1998). *Neuroscience* 82:7–19.
Stabler, S. M. et al. (1999). *J Cell Biol* 145:1277–1292.
Stahl, B. et al. (1999). *J Biol Chem* 274:9141–9148.
Stathakis D G et al. (1997). *Genomics* 44:71–82.
Storey, E. and Cappai, R. (1999). *Neuropathol Appl Neurobiol* 25:81–97.
Strickland, D. K. et al. (1991). *J Biol Chem* 266:13364–13369.
Su, J. H. et al. (1997). *J Neuropathol Exp Neurol* 56:86–93.
Sugaya, K. et al. (1998). *Neurobiol Aging* 19:351–361.
Takagi, N. et al. (2000). *J Neurochem* 74:169–178.
Tamura, M. et al. (1999). *J Biol Chem* 274:20693–20703.
Tanahashi, H. and Tabira, T. (1999). *Neuroreport* 10:563–568.
Tesco, G. et al. (1998). *J Biol Chem* 273:33909–33914.
Thinakaran, G. et al. (1997). *J Biol Chem* 272:28415–28422.
Tomita, S. et al. (1999). *J Biol Chem* 274:2243–2254.
Tomita, T. et al. (1997). *Proc Natl Acad Sci USA* 94:2025–2030.
Trommsdorff, M et al. (1998). *J Biol Chem* 273:33556–33560.
Ullrich, O. et al. (1996). *J Cell Biol* 135:913–924.
Urbe, S. et al. (1993). *FEBS Lett* 334:175–182.
Van Leuven, F. et al. (1995). *Genomics* 25:492–500.
Vassar, R. et al. (1999). *Science* 286:735–741.
Villacres, E. C. et al. (1998). *J Neurosci* 18:3186–3194.
Virsolvy-Vergine, A. et al. (1992). *Proc Natl Acad Sci USA* 89:6629–6633.
Vito, P. et al. (1996). *J Biol Chem* 271:31025–31028.
Wallace, W. C. et al. (1997a). *Brain Res Mol Brain Res* 52:201–212.
Wallace, W. C. et al. (1997b). *Brain Res Mol Brain Res* 52:213–227.
Walton, M. et al. (1999). *J Neurosci Res* 58:96–106.
Wang, L. H. et al. (1999). *J Biol Chem* 274:14137–14146.
Webster, S. et al. (1997). *J Neurochem* 69:388–398.
Weiss, J. H. et al (1994). *J Neurochem* 62:372–375.
Wetmur, J. G. and Davidson, N. (1968). *J. Mol. Biol.* 31:349–370.
Wheal H V et al. (1998). *Prog Neurobiol* 55:611–40.
Whitehouse, P. J. (1997). *Neurology* 48 Suppl. 7:S2–S7.
Williamson, T. G. et al. (1996). *J Biol Chem* 271:31215–31221.
Willnow, T. E. et al. (1996). *EMBO J* 15:2632–2639.
Willnow, T. E. et al. (1995). *Proc Natl Acad Sci USA* 92:4537–4541.
Wolfe, M. S. et al. (1999a). *Biochemistry* 38:11223–11230.
Wolfe, M. S. et al. (1999b). *Nature* 398:513–517.
Wolozin, B. et al. (1996). *Science* 274:1710–1713.
Wong, W. T. et al. (1994). *Oncogene* 9:3057–3061.
Xie, C. et al. (1998). *Free Radic Biol Med* 25:979–988.
Yamamoto, K. et al. (1994). *J Neurobiol* 25:585–594.
Yan, R. et al. (1999). *Nature* 402:533–537.
Ye, J. et al. (2000). *Proc Natl Acad Sci USA* 97:5123–5128.
Yeo, T. T. et al. (1997). *J Neurosci Res* 47:348–360.
Yu, G. et al. (1998). *J Biol Chem* 273:16470–16475.
Yu, G. et al. (2000a). *J Biol Chem* 275:27348–27353.
Yu, G. et al. (2000b). *Nature* 407:48–54.
Yu, H. et al. (1996). *J Biol Chem* 271:29993–29998.
Zachary, I. (1997). *Int J Biochem Cell Biol* 29:929–934.
Zambrano, N. et al. (1998). *J Biol Chem* 273:20128–20133.
Zawar, C. and Neumcke, B. (2000). *Pflugers Arch* 439:256–262.
Zawar, C. et al. (1999). *J Physiol* 514:327–341.
Zhang, C. et al. (1994). *J Biol Chem* 269:25247–25250.
Zhang, Z. et al. (1998). *Nature* 395:698–702.
Zhou, J. H. et al. (1997a). *Neuroreport* 8:2085–2090.
Zhou, J. H. et al. (1997b). *Neuroreport* 8:1489–1494
Zlokovic, B. V. et al. (1996). *Proc Natl Acad Sci USA* 93:4229–4234.
PCT Published Application No. WO 97/27296
PCT Published Application No. WO 99/65939
U.S. Pat. No. 5,622,852
U.S. Pat. No. 5,773,218

What is claimed is:

1. An isolated nucleic acid sequence comprising a nucleotide sequence set forth in SEQ ID NO:3, or the complement thereof.

2. A nucleic acid vector comprising the isolated nucleic acid of claim 1.

3. An isolated host cell comprising the isolated nucleic acid of claim 1.

4. A method for making an isolated polypeptide comprising an amino acid sequence set forth in SEQ ID NO:4, comprising:
   providing an expression vector comprising a nucleic acid encoding said amino acid sequence; and
   introducing said expression vector into a host cell such that said host cell produces the isolated polypeptide.

* * * * *

SEQUENCE LISTING

<160> NUMBER OF SEQ ID NOS: 8

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence:tail for
    forward primer for yeast two-hybrid system

<400> SEQUENCE: 1
gcaggaaaca gctatgacca tacagtcagc ggccgccacc                                40

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence:tail for
      reverse primer for yeast two-hybrid system

<400> SEQUENCE: 2
acggccagtc gcgtggagtg ttatgtcatg cggccgcta                                 39

<210> SEQ ID NO 3
<211> LENGTH: 2740
<212> TYPE: DNA
<213> ORGANISM: Homo sapiens
<220> FEATURE:
<221> NAME/KEY: CDS
<222> LOCATION: (217)..(1332)

<400> SEQUENCE: 3
cgagaatttc cagcaggcaa ggcagtggcc gctttgactg cttgcttcgg agatccgaga          60
cgacggagaa ggcactctta tttaccgacc aagaaagctc ctccccgtc ctccgttagc         120 taattaaaac attttcagg gacgtagcca tccagagaca ttccattatt gttccattga         180
cctttccctc atcactgagt cctttggagc tgagtt atg tca aca gct gcc tta          234
                                        Met Ser Thr Ala Ala Leu
                                         1               5 att act ttg gtc aga agt ggt ggg aac cag gtg aga agg aga gtg ctg          282
Ile Thr Leu Val Arg Ser Gly Gly Asn Gln Val Arg Arg Arg Val Leu
        10                  15                  20 cta agc tcc cgc ctg ctg cag gac gac agg cgg gtg aca ccc acg tgc          330
Leu Ser Ser Arg Leu Leu Gln Asp Asp Arg Arg Val Thr Pro Thr Cys
    25                  30                  35 cac agc tcc act tca gag cct agg tgt tct cgg ttt gac cca gat ggt          378
His Ser Ser Thr Ser Glu Pro Arg Cys Ser Arg Phe Asp Pro Asp Gly
40                  45                  50 agt ggg agt cca gct acc tgg gac aat ttt ggg atc tgg gat aac cgc          426
Ser Gly Ser Pro Ala Thr Trp Asp Asn Phe Gly Ile Trp Asp Asn Arg
55                  60                  65                  70 att gat gag cca att ctg ctg cca ccc agc att aag tat ggc aag cca          474
Ile Asp Glu Pro Ile Leu Leu Pro Pro Ser Ile Lys Tyr Gly Lys Pro
            75                  80                  85 att ccc aaa atc agc ttg gaa aat gtg ggg tgc gcc tca cag att ggc          522
Ile Pro Lys Ile Ser Leu Glu Asn Val Gly Cys Ala Ser Gln Ile Gly
        90                  95                 100 aaa cgg aaa gag aat gaa gat cgg ttt gac ttc gct cag ctg aca gat          570
Lys Arg Lys Glu Asn Glu Asp Arg Phe Asp Phe Ala Gln Leu Thr Asp
    105                 110                 115 gag gtc ctg tac ttt gca gtg tat gat gga cac ggt gga cct gca gca          618
Glu Val Leu Tyr Phe Ala Val Tyr Asp Gly His Gly Gly Pro Ala Ala
        120                 125                 130 gct gat ttc tgt cat acc cac atg gag aaa tgt att atg gat ttg ctt          666
Ala Asp Phe Cys His Thr His Met Glu Lys Cys Ile Met Asp Leu Leu
135                 140                 145                 150 cct aag gag aag aac ttg gaa act ctg ttg acc ttg gct ttt cta gaa          714
Pro Lys Glu Lys Asn Leu Glu Thr Leu Leu Thr Leu Ala Phe Leu Glu
            155                 160                 165

| | | |
|---|---|---|
| ata gat aaa gcc ttt tcg agt cat gcc cgc ctg tct gct gat gca act<br>Ile Asp Lys Ala Phe Ser Ser His Ala Arg Leu Ser Ala Asp Ala Thr<br>170 175 180 | | 762 |
| ctt ctg acc tct ggg act act gca aca gta gcc cta ttg cga gat ggt<br>Leu Leu Thr Ser Gly Thr Thr Ala Thr Val Ala Leu Leu Arg Asp Gly<br>185 190 195 | | 810 |
| att gaa ctg gtt gta gcc agt gtt ggg gac agc cgg gct att ttg tgt<br>Ile Glu Leu Val Val Ala Ser Val Gly Asp Ser Arg Ala Ile Leu Cys<br>200 205 210 | | 858 |
| aga aaa gga aaa ccc atg aag ctg acc att gac cat act cca gaa aga<br>Arg Lys Gly Lys Pro Met Lys Leu Thr Ile Asp His Thr Pro Glu Arg<br>215 220 225 230 | | 906 |
| aaa gat gaa aaa gaa agg atc aag aaa tgt ggt ggt ttt gta gct tgg<br>Lys Asp Glu Lys Glu Arg Ile Lys Lys Cys Gly Gly Phe Val Ala Trp<br>235 240 245 | | 954 |
| aat agt ttg ggg cag cct cac gta aat ggc agg ctt gca atg aca aga<br>Asn Ser Leu Gly Gln Pro His Val Asn Gly Arg Leu Ala Met Thr Arg<br>250 255 260 | | 1002 |
| agt att gga gat ttg gac ctt aag acc agt ggt gtc ata gca gaa cct<br>Ser Ile Gly Asp Leu Asp Leu Lys Thr Ser Gly Val Ile Ala Glu Pro<br>265 270 275 | | 1050 |
| gaa act aag agg att aag tta cat cat gct gat gac agc ttc ctg gtc<br>Glu Thr Lys Arg Ile Lys Leu His His Ala Asp Asp Ser Phe Leu Val<br>280 285 290 | | 1098 |
| ctc acc aca gat gga att aac ttc atg gtg aat agt caa gag att tgt<br>Leu Thr Thr Asp Gly Ile Asn Phe Met Val Asn Ser Gln Glu Ile Cys<br>295 300 305 310 | | 1146 |
| gac ttt gtc aat cag tgc cat gat ccc aac gaa gca gcc cat gcg gtg<br>Asp Phe Val Asn Gln Cys His Asp Pro Asn Glu Ala Ala His Ala Val<br>315 320 325 | | 1194 |
| act gaa cag gca ata cag tac ggt act gag gat aac agt act gca gta<br>Thr Glu Gln Ala Ile Gln Tyr Gly Thr Glu Asp Asn Ser Thr Ala Val<br>330 335 340 | | 1242 |
| gta gtg cct ttt ggt gcc tgg gga aaa tat aag aac tct gaa atc aac<br>Val Val Pro Phe Gly Ala Trp Gly Lys Tyr Lys Asn Ser Glu Ile Asn<br>345 350 355 | | 1290 |
| ttc tca ttc agc aga agc ttt gcc tcc agt gga cga tgg gcc<br>Phe Ser Phe Ser Arg Ser Phe Ala Ser Ser Gly Arg Trp Ala<br>360 365 370 | | 1332 |
| tgattaccag ctgggactta gagtttctgt gcaacagttt ttcactgagc atgtcaagaa | | 1392 |
| actgataaga tcaaaaaggt ctcctaactc actagatcag cgcacaagtc agtgtaaacc | | 1452 |
| acttagatag tagttttttc ataaatgctc atcatattta tgttccgctg tacatgttca | | 1512 |
| gtataaatat atgtgtagtg aagctactgt gagtctttaa atggaaagag caaatgagaa | | 1572 |
| gtggttttgga tacacttgat gagagatgag agtgtcacat taataatttt taagactctt | | 1632 |
| aggcagctat gggtttcttt tgatcatttt tgttctttat tcatttgaac acgttttga | | 1692 |
| agttcttcaa aactagtcag tttgaatttt gacagctatt caatatgtga tctccaagtt | | 1752 |
| taaaaaaatt ttttccaga cttccctaat cctaaaatgc gagttttat ttttaataac | | 1812 |
| tgtaccaagg aataagtatg aaaacagttc tctgttacca tattttgtat tctggaccac | | 1872 |
| ttactggtga aagcaaccat gcaaaagaaa ttaatttggc caggcacagt ggctcatgcc | | 1932 |
| tgtaatccca aattgctggg attacagcac tgtgccctcc taggaaatta ttttttaagt | | 1992 |
| gaaattttat ttttattttt ttaggattt tggtagagaa tgagtaggcc tactcatcaa | | 2052 |
| tatcaaacag gacatttagt ttctttcctt agaacagaca taaatttaat ttcatggtaa | | 2112 |
| tatgataata agaaaatgct tctatttttc tttagcacct ccatggttct catatcccca | | 2172 |

-continued

```
tgtctgtaaa aagtgacatg agaattttgt tgggttacat tttattgtat ttattagatt      2232
cgcttatata gatgacttag gcagaaataa agtcatgtct ttagaaggtg aacaagccaa      2292
cttgtgatgg cctgccttt  gcttttggca gttgggatga aacaattga  ctctcccatt      2352 ggttgttaga tagttgaaat ggtgcgttgg tggtcatact tagtgttcta ggctgtgaaa      2412
tcatggagtt cttccacttc caagaatgac tcatttgctg ttggattcta gtacagaatt      2472
tagcagcctg atgtgtcccc aaactgattt aatttctact gaagtgccct tgtgtacatt      2532
tgttttgtaa tttaccaaag tactacctga gtgtataatg actcctgcag tgagttaatg      2592
taattgctgc tttgaccatt gttttaaatc tgtgtactag agtaactgtg agcagaatga      2652
aatcacatta tctcagtgtt caaaatatca ttctaataaa gtacatgcat taaacaattt      2712
taaaaaaaac aaaaaaaaaa aaaaaaa                                          2740
```

<210> SEQ ID NO 4
<211> LENGTH: 372
<212> TYPE: PRT
<213> ORGANISM: Homo sapiens

<400> SEQUENCE: 4

```
Met Ser Thr Ala Ala Leu Ile Thr Leu Val Arg Ser Gly Gly Asn Gln
 1               5                  10                  15
Val Arg Arg Arg Val Leu Leu Ser Ser Arg Leu Leu Gln Asp Asp Arg
                20                  25                  30
Arg Val Thr Pro Thr Cys His Ser Ser Thr Ser Glu Pro Arg Cys Ser
            35                  40                  45
Arg Phe Asp Pro Asp Gly Ser Gly Ser Pro Ala Thr Trp Asp Asn Phe
        50                  55                  60
Gly Ile Trp Asp Asn Arg Ile Asp Glu Pro Ile Leu Leu Pro Pro Ser
    65                  70                  75                  80
Ile Lys Tyr Gly Lys Pro Ile Pro Lys Ile Ser Leu Glu Asn Val Gly
                85                  90                  95
Cys Ala Ser Gln Ile Gly Lys Arg Lys Glu Asn Glu Asp Arg Phe Asp
               100                 105                 110
Phe Ala Gln Leu Thr Asp Glu Val Leu Tyr Phe Ala Val Tyr Asp Gly
           115                 120                 125
His Gly Gly Pro Ala Ala Ala Asp Phe Cys His Thr His Met Glu Lys
       130                 135                 140
Cys Ile Met Asp Leu Leu Pro Lys Glu Lys Asn Leu Glu Thr Leu Leu
145                 150                 155                 160
Thr Leu Ala Phe Leu Glu Ile Asp Lys Ala Phe Ser Ser His Ala Arg
               165                 170                 175
Leu Ser Ala Asp Ala Thr Leu Leu Thr Ser Gly Thr Thr Ala Thr Val
           180                 185                 190
Ala Leu Leu Arg Asp Gly Ile Glu Leu Val Val Ala Ser Val Gly Asp
       195                 200                 205
Ser Arg Ala Ile Leu Cys Arg Lys Gly Lys Pro Met Lys Leu Thr Ile
   210                 215                 220
Asp His Thr Pro Glu Arg Lys Asp Glu Lys Glu Arg Ile Lys Lys Cys
225                 230                 235                 240
Gly Gly Phe Val Ala Trp Asn Ser Leu Gly Gln Pro His Val Asn Gly
               245                 250                 255
Arg Leu Ala Met Thr Arg Ser Ile Gly Asp Leu Asp Leu Lys Thr Ser
           260                 265                 270
Gly Val Ile Ala Glu Pro Glu Thr Lys Arg Ile Lys Leu His His Ala
       275                 280                 285
Asp Asp Ser Phe Leu Val Leu Thr Thr Asp Gly Ile Asn Phe Met Val
   290                 295                 300
Asn Ser Gln Glu Ile Cys Asp Phe Val Asn Gln Cys His Asp Pro Asn
305                 310                 315                 320
Glu Ala Ala His Ala Val Thr Glu Gln Ala Ile Gln Tyr Gly Thr Glu
               325                 330                 335
Asp Asn Ser Thr Ala Val Val Pro Phe Gly Ala Trp Gly Lys Tyr
           340                 345                 350
Lys Asn Ser Glu Ile Asn Phe Ser Phe Ser Arg Ser Phe Ala Ser Ser
       355                 360                 365
Gly Arg Trp Ala
   370
```

```
<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:tail for
      forward primer for yeast two-hybrid system

<400> SEQUENCE: 5
ccgccaccat ggaatta                                                  17

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence:tail for
      reverse primer for yeast two-hybrid system

<400> SEQUENCE: 6
tgcggccgct agtcga                                                   16

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:secondary
      forward primer for yeast two-hybrid system

<400> SEQUENCE: 7
cgcaggaaac agctatga                                                 18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:secondary
      reverse primer for yeast two-hybrid system

<400> SEQUENCE: 8
ttctaaaacg acggccag                                                 18
```